(12) United States Patent
Pan et al.

US010840450B2

(10) Patent No.: US 10,840,450 B2
(45) Date of Patent: Nov. 17, 2020

(54) POLYMER, AND MIXTURE OR FORMULATION, AND ORGANIC ELECTRONIC DEVICE CONTAINING SAME, AND MONOMER THEREOF

(71) Applicant: GUANGZHOU CHINARAY OPTOELECTRONIC MATERIALS LTD., Guangdong (CN)

(72) Inventors: Junyou Pan, Guangdong (CN); Hong Huang, Guangdong (CN)

(73) Assignee: GUANGZHOU CHINARAY OPTOELECTRONIC MATERIALS LTD., Guangdong (CN)

( * ) Notice: Subject to any disclaimer, the term of this patent is extended or adjusted under 35 U.S.C. 154(b) by 666 days.

(21) Appl. No.: 15/532,883

(22) PCT Filed: Dec. 3, 2015

(86) PCT No.: PCT/CN2015/096328
§ 371 (c)(1),
(2) Date: Aug. 28, 2017

(87) PCT Pub. No.: WO2016/086886
PCT Pub. Date: Jun. 9, 2016

(65) Prior Publication Data
US 2017/0358751 A1 Dec. 14, 2017

(30) Foreign Application Priority Data
Dec. 4, 2014 (CN) .......................... 2014 1 0734855

(51) Int. Cl.
| | | |
|---|---|---|
| *H01L 51/00* | (2006.01) | |
| *C09K 11/06* | (2006.01) | |
| *C08F 12/26* | (2006.01) | |
| *C08F 12/22* | (2006.01) | |
| *C09D 125/18* | (2006.01) | |
| *C08F 212/32* | (2006.01) | |
| *C08F 12/32* | (2006.01) | |
| *C07D 219/02* | (2006.01) | |
| *C07D 413/10* | (2006.01) | |
| *C07C 49/798* | (2006.01) | |
| *C07D 487/04* | (2006.01) | |
| *C07C 13/00* | (2006.01) | |
| *C07C 13/72* | (2006.01) | |
| *C07D 209/86* | (2006.01) | |
| *C08F 12/00* | (2006.01) | |

(52) U.S. Cl.
CPC .......... *H01L 51/0035* (2013.01); *C07C 13/00* (2013.01); *C07C 13/72* (2013.01); *C07C 49/798* (2013.01); *C07D 209/86* (2013.01); *C07D 219/02* (2013.01); *C07D 413/10* (2013.01); *C07D 487/04* (2013.01); *C08F 12/00* (2013.01); *C08F 12/22* (2013.01); *C08F 12/26* (2013.01); *C08F 12/32* (2013.01); *C08F 212/32* (2013.01); *C09D 125/18* (2013.01); *C09K 11/06* (2013.01); *H01L 51/0071* (2013.01); *C07C 2602/50* (2017.05); *C07C 2603/18* (2017.05); *C09K 2211/00* (2013.01); *C09K 2211/14* (2013.01)

(58) Field of Classification Search
CPC .. C09K 11/06; C09K 2211/14; C09K 2211/00
See application file for complete search history.

(56) References Cited

U.S. PATENT DOCUMENTS

| | | | |
|---|---|---|---|
| 3,567,450 | A | 3/1971 | Brantley et al. |
| 3,615,404 | A | 10/1971 | Price et al. |
| 4,720,432 | A | 1/1988 | VanSlyke et al. |
| 4,769,292 | A | 9/1988 | Tang et al. |
| 5,061,569 | A | 10/1991 | VanSlyke et al. |
| 5,121,029 | A | 6/1992 | Hosokawa et al. |
| 5,130,603 | A | 7/1992 | Tokailin et al. |
| 6,020,078 | A | 2/2000 | Chen et al. |
| 6,251,531 | B1 | 6/2001 | Enokida et al. |
| 6,824,895 | B1 | 11/2004 | Sowinski et al. |
| 6,830,828 | B2 | 12/2004 | Thompson et al. |
| 6,835,469 | B2 | 12/2004 | Kwong et al. |
| 7,029,766 | B2 | 4/2006 | Huo et al. |
| 7,250,532 | B2 | 7/2007 | Iwakuma et al. |
| 7,767,317 | B2 | 8/2010 | Begley et al. |

(Continued)

FOREIGN PATENT DOCUMENTS

| | | |
|---|---|---|
| CN | 1583691 | 2/2005 |
| CN | 101123301 A | 2/2008 |

(Continued)

OTHER PUBLICATIONS

Ying et al, "Flat Panel Display Technology", Dec. 2002, pp. 359-360.*
Uoyama et al, "Highly Efficient Oreganic Light-Emiting Diodes From Delayed Fluorescence", Nature, vol. 492, Dec. 13, 2012, pp. 234-238.*
Extended European Search Report issued for European Patent Application No. 15865073.9, dated Jul. 13, 2018, 5 pages.

(Continued)

*Primary Examiner* — C Melissa Koslow
(74) *Attorney, Agent, or Firm* — Hamre, Schumann, Mueller & Larson, P.C.

(57) ABSTRACT

Disclosed are a polymer, and a mixture or a formulation and an organic electronic device containing same, and applications thereof, and further a monomer of which the polymer is made; the polymer comprises on its side chain a repeating structure unit E, characterizing in that its S1(E)−T1(E)) ≤0.35 eV or even less, which may allow the said polymer having thermally activated delayed fluorescence (TADF) property. Thus a TADF polymer suitable for printing processes is provided, thereby reducing OLED manufacturing costs.

11 Claims, No Drawings

(56) References Cited

U.S. PATENT DOCUMENTS

| | | | |
|---|---|---|---|
| 10,312,452 B2* | 6/2019 | Kimura | C07C 211/58 |
| 2001/0053462 A1 | 12/2001 | Mishima | |
| 2005/0222352 A1* | 10/2005 | Litz | H05B 33/14 |
| | | | 526/259 |
| 2005/0258742 A1 | 11/2005 | Tsai et al. | |
| 2006/0210830 A1 | 9/2006 | Funahashi et al. | |
| 2006/0222886 A1 | 10/2006 | Kwong et al. | |
| 2006/0251923 A1 | 11/2006 | Lin et al. | |
| 2007/0087219 A1 | 4/2007 | Ren et al. | |
| 2007/0092753 A1 | 4/2007 | Begley et al. | |
| 2007/0252517 A1 | 11/2007 | Owczarczyk et al. | |
| 2008/0027220 A1 | 1/2008 | Stossel et al. | |
| 2008/0113101 A1 | 5/2008 | Inoue et al. | |
| 2009/0061681 A1 | 3/2009 | McMunigal et al. | |
| 2009/0096363 A1 | 4/2009 | Burroughes et al. | |
| 2009/0134784 A1 | 5/2009 | Lin et al. | |
| 2011/0284799 A1 | 11/2011 | Stossel et al. | |

FOREIGN PATENT DOCUMENTS

| | | |
|---|---|---|
| CN | 102282150 | 12/2011 |
| CN | 103531062 A | 1/2014 |
| CN | 103985822 | 8/2014 |
| DE | 102005058557 | 6/2007 |
| EP | 1144543 | 3/2004 |
| EP | 1191613 | 3/2006 |
| EP | 1191614 | 5/2009 |
| EP | 1191612 | 9/2009 |
| EP | 1941562 | 5/2010 |
| EP | 1957606 | 11/2017 |
| JP | 2913116 | 6/1999 |
| JP | 2008053397 | 3/2008 |
| WO | 00/70655 | 11/2000 |
| WO | 01/21729 | 3/2001 |
| WO | 01/41512 | 6/2001 |
| WO | 02/02714 | 1/2002 |
| WO | 02/15645 | 2/2002 |
| WO | 2005/019373 | 3/2005 |
| WO | 2005/033244 | 4/2005 |
| WO | 2006/000388 | 1/2006 |
| WO | 2006/000389 | 1/2006 |
| WO | 2006/058737 | 6/2006 |
| WO | 2006/122630 | 11/2006 |
| WO | 2007/065549 | 6/2007 |
| WO | 2007/095118 | 8/2007 |
| WO | 2007/115610 | 10/2007 |
| WO | 2007/140847 | 12/2007 |
| WO | 2008/006449 | 1/2008 |
| WO | 2009/118087 | 10/2009 |
| WO | 2009/146770 | 12/2009 |
| WO | 2010/015307 | 2/2010 |
| WO | 2010/031485 | 3/2010 |
| WO | 2010/054728 | 5/2010 |
| WO | 2010/054731 | 5/2010 |
| WO | 2010/086089 | 8/2010 |
| WO | 2010/099852 | 9/2010 |
| WO | 2010/102709 | 9/2010 |
| WO | 2010/135519 | 11/2010 |
| WO | 2011/110277 | 9/2011 |
| WO | 2011/141110 | 11/2011 |
| WO | 2011/157339 | 12/2011 |
| WO | 2012/004407 | 1/2012 |
| WO | 2012/007086 | 1/2012 |
| WO | 2012/007087 | 1/2012 |
| WO | 2012/007088 | 1/2012 |
| WO | 2014166584 A1 | 10/2014 |
| WO | 2014166585 A1 | 10/2014 |
| WO | WO 2015090177 * | 6/2015 |

OTHER PUBLICATIONS

First Office Action and Search Report issued for Chinese Patent Application No. 201580065947.3, dated Apr. 13, 2018, 11 pages (including partial English translation).

Ying et al., "Flat Panel Display Technology," Dec. 31, 2002, pp. 359-360, Post & Telecom Press, China (including partial English translation).

C. Adachi et al., "High-efficiency red electrophosphorescence devices," Applied Physics Letters, vol. 78, No. 11 (2001), p. 1622-1624.

M. A. Baldo et al., "High-efficiency fluorescent organic light-emitting devices using a phosphorescent sensitizer," Nature, vol. 403 (2000), p. 750-753.

V. Bulovic et al., "Transparent light-emitting devices," Nature, vol. 380 (1996), p. 29.

G. Gu et al., "Transparent organic light emitting devices," Appl. Phys. Lett., vol. 68, No. 19 (1996), p. 2606-2608.

C. E. Johnson et al., "Luminescent Iridium(I), Rhodium(I), and Platinum(II) Dithiolate Complexes," J. Am. Chem. Soc., vol. 105 (1983), p. 1795-1802.

J. Kido et al., "Bright red light-emitting organic electroluminescent devices having a europium complex as an emitter," Appl. Phys. Lett., vol. 65 (1994), p. 2124-2126.

J. Kido et al., "Electroluminescence in a Terbium Complex" Chemistry Letters (1990), p. 657-660.

H. Kipphan, Excerpt of "Handbook of Print Media," Springer-Verlag Berlin Heidelberg, (2001) 13 pages.

Y. Ma et al., "Electroluminescence from triplet metal-ligand charge-transfer excited state of transition metal complexes," Synthetic Metals, vol. 94 (1998), p. 245-248.

H. Uoyama et al., "Highly efficient organic light-emitting diodes from delayed fluorescence," Nature, vol. 492 (2012), p. 234-238.

M. Wrighton and D.L Morse, "The Nature of the Lowest Excited State in Tricarbonylchloro-1,10-phenanthrolinerhenium(I) and Related Complexes," Journal of the American Chemical Society, vol. 96, No. 4 (1974), p. 998-1003.

G. R. Newkome et al., "Dendrimers and Dendrons: Concepts, Syntheses, Applications," Wiley-VCH, ISBN: 3527299971, 2002 (320 pages).

International Search Report for international appl. No. PCT/CN2015/096328, dated Feb. 23, 2016 (2 pages).

* cited by examiner

POLYMER, AND MIXTURE OR FORMULATION, AND ORGANIC ELECTRONIC DEVICE CONTAINING SAME, AND MONOMER THEREOF

TECHNICAL FIELD

The present disclosure relates to the field of electroluminescent materials, and in particular to a polymer; a mixture or a formulation and an organic electronic device containing the same; and a monomer that can form the polymer.

BACKGROUND

Organic light-emitting diodes (OLEDs) made of organic semiconductor materials have a great potential in the applications of novel optoelectronic devices such as in the applications of flat panel displays and lighting because of the synthetic diversity, low manufacturing cost, and high optical and electrical performance of organic semiconductive materials, making it possible to manufacture a large-scale flexible device. In order to improve the luminous efficiency of organic light-emitting diodes, various systems of light emitter materials based on fluorescence and phosphorescence have been developed. The organic light-emitting diode employing the fluorescent material has achieved quite a high performance, for example, almost an internal luminescence quantum efficiency of 100%. However, so far, the phosphorescent materials which have a practical value are iridium and platinum complexes; the cost is quite high since the raw material is rare and expensive and the synthesis of the complex is rather complicated. Adachi proposed the concept of reverse intersystem crossing so that an organic compound can be used, i.e. without using the metal complex, to achieve a high efficiency of phosphorescent OLED. This may come true by thermal activated delayed fluorescent material TADF, see Adachi et al., Nature Vol 492, 234, (2012).

In order to take full advantage of organic materials, it is desirable to prepare OLEDs by printing at low cost and in large area. Reported existing TADF materials have a relatively low molecular weight and does not facilitates the printing process since it is not easy to adjust the solubility as well as the important parameters for the printing process, such as viscosity, surface tension.

A new material system suitable for the printing has yet to be developed.

SUMMARY OF THE INVENTION

In view of the above-mentioned deficiencies of the prior art, it is an object of the present disclosure to provide a polymer, a mixture, a formulation, and an organic electronic device containing the same and its monomer, which aim to provide a new polymer material, and solve the problem that the existing TADF materials is not suitable for the printing process.

In one aspect of the present disclosure, there is provided a polymer containing a repeating unit represented by chemical formula 1, wherein the energy difference between the singlet energy level and the triplet energy level of the structural unit E, i.e. (S1(E)–T1(E)), is less than or equal to 0.35 eV

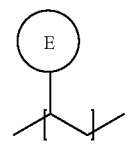

Chemical Formula 1

According to one of the embodiments of the present disclosure, there is provided the polymer as described above, wherein E is an organic compound containing at least one electron donating group D and at least one electron accepting group A, and (S1(E)–T1(E))≤0.35 eV In some preferred embodiments, E is an organic compound having the following structural formula (I):

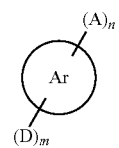

(I)

Wherein Ar is an aromatic or heteroaromatic structural unit, D is an electron donating group, A is an electron accepting group, n and m are an integer between 1 and 6 respectively; wherein when m>1, each D is independently of each other selected from the same or different electron donating groups, and when n>1, each A is independently of each other selected from the same or different electron accepting groups.

According to another aspect of the present disclosure, there is provided a formulation containing the polymer as described above and at least one organic solvent.

According to another aspect of the present disclosure, a mixture is provided. The mixture contains the polymer as described above, and at least one organic functional material that is selected from the group consisting of a hole-injecting or hole-transporting material, a hole-blocking material, an electron-injecting or electron-transporting material, an electron-blocking material, an organic host material, a singlet emitter, and a triplet emitter.

According to another aspect of the present disclosure, there is provided the use of the polymer as described above in an organic electronic device.

According to further aspect of the present disclosure, there is provided an organic electronic device containing at least the polymer as described above.

According to another aspect of the present disclosure, there is provided a polymerizable monomer having the following general formula:

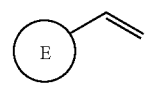

wherein the difference between the singlet energy level and the triplet energy level of the structural unit E, (S1(E)–T1(E))≤0.35 eV.

The present disclosure has the advantages that the polymer of the present disclosure has a high molecular weight, good solubility in organic solvent and good film-forming property, so as to provide a better solution for the materials for printing OLED.

DETAILED DESCRIPTION OF THE EMBODIMENTS

The present disclosure provides a polymer and its application in organic electroluminescent devices, as well as the organic electronic device containing the polymer and its preparation method. The present disclosure will now be described in greater detail with reference to the accompanying drawings so that the purpose, technical solutions, and technical effects thereof are more clear and comprehensible. It is to be understood that the specific embodiments described herein are merely illustrative of, and are not intended to limit, the disclosure.

The polymer provided in the present disclosure containing a repeating unit represented by chemical formula 1, wherein the energy difference between the singlet energy level and the triplet energy level of the structural unit E, i.e. (S1(E)–T1(E)), is less than or equal to 0.35 eV.

Chemical Formula 1

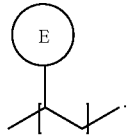

In an embodiment of the present disclosure, triplet energy level (T1), singlet energy level (S1), HOMO, and LUMO play a key role in the energy level structure of the organic material. First of all, the determination of these energy levels is introduced as follows.

HOMO and LUMO energy levels can be measured by photoelectric effects, such as XPS (X-ray photoelectron spectroscopy) and UPS (UV photoelectron spectroscopy), or by cyclic voltammetry (hereinafter referred to as CV). Recently, quantum chemical method, such as density functional theory (hereinafter referred to as DFT), has also become an effective method for calculating the molecular orbital energy levels.

The triplet energy level T1 of an organic material can be measured by a low-temperature time-resolved spectroscopy or by quantum simulation calculation (for example, by Time-Dependent DFT), such as by commercial software Gaussian 03W (Gaussian Inc.). Detailed simulation methods can be found in WO2011141110.

The singlet energy level Si of an organic material can be determined by the absorption spectrum or the emission spectrum, and can also be obtained by quantum simulation calculation (such as Time-dependent DFT).

It should be noted that the absolute values of HOMO, LUMO, T1 and S1 depend on the measurement method or calculation method used, and even for the same method but different evaluation method, for example, different HOMO/LUMO value can be provided at the start point and peak point on a CV curve. Therefore, a reasonable and meaningful comparison should be carried out by using the same measurement method and the same evaluation method. As described in the embodiments of the present disclosure, the values of HOMO, LUMO, T1 and S1 are based on time-dependent DFT simulation without affecting the application of other measurement or calculation methods.

The polymer according to the invention has an advantage that the repeating unit E is linked by the backbone of a non-conjugated polymer to realize a higher molecular weight while keeping the energy structure of a single repeating unit, i.e., HOMO, LUMO, S1 and T1 of the single repeating unit essentially unchanged.

In some preferred embodiments, (S1(E)–T1(E))≤0.30 eV, preferably ≤0.25 eV, more preferably ≤0.20 eV, even more preferably ≤0.15 eV, most preferably ≤0.10 eV.

According to the polymer of the present disclosure, E is an emitter. In general, the emitter has a range of proportion in the light-emitting layer. In some embodiments, the repeating unit E may be present in an amount of from 0.1 mol % to 90 mol % in the polymer.

In a preferred embodiment, the repeating unit E may be present in an amount of from 0.1 mol % to 80 mol %, preferably from 2 mol % to 70 mol %, more preferably from 3 mol % to 50 mol %, even more preferably from 3 mol % to 30 mol %, most preferably from 4 mol % to 20 mol % in the polymer.

In the embodiments of the present disclosure, the main material, the matrix material, the host material and the matrix material have the same meaning and are interchangeable.

In the embodiments of the present disclosure, singlet and singlet state have the same meaning and can be interchanged.

In the embodiments of the present disclosure, triplet and triplet state have the same meaning and can be interchanged.

As used herein, the term "small molecule" refers to a molecule that is not a polymer, oligomer, dendrimer, or blend. In particular, there is no repetitive structure in small molecules. The molecular weight of the small molecule is no greater than 3000 g/mole, more preferably no greater than 2000 g/mole, and most preferably no greater than 1500 g/mole.

Polymer includes homopolymer, copolymer, and block copolymer. In addition, in the present disclosure, the polymer also includes dendrimer. The synthesis and application of dendrimers are described in Dendrimers and Dendrons, Wiley-VCH Verlag GmbH & Co. KGaA, 2002, Ed. George R. Newkome, Charles N. Moorefield, Fritz Vogtle.

Conjugated polymer is a polymer whose backbone is predominantly composed of the sp2 hybrid orbital of carbon (C) atom. Some known examples are: polyacetylene and poly (phenylene vinylene), on the backbone of which the C atom can also be optionally substituted by other non-C atoms, and which is still considered to be a conjugated polymer when the sp2 hybridization on the backbone is interrupted by some natural defects. In addition, the conjugated polymer in the present disclosure may also comprise aryl amine, aryl phosphine and other heteroarmotics, organometallic complexes, and the like on the backbone.

The polymer according to the present disclosure is a non-conjugated polymer.

In a preferred embodiment, the repeating structural unit E of the polymer according to the present disclosure is a structural unit that contains at least one electron donating group D and at least one electron accepting group A.

In a more preferred embodiment, the repeating structural unit E of the polymer according to the present disclosure is a structural unit containing the following structural formula (I):

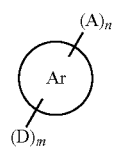

(I)

Wherein Ar is an aromatic or heteroaromatic structural unit, D is an electron donating group, A is an electron accepting group, n and m are an integer between 1 and 6 respectively; wherein when m>1, each D is independently of each other selected from the same or different electron donating groups, and when n>1, each A is independently of each other selected from the same or different electron accepting groups.

Suitable electron donating group D may be selected from groups having any backbone of the following general formulas 1-3:

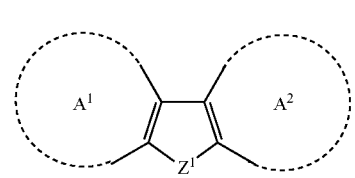

General Formula 1

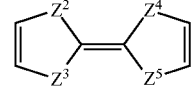

General Formula 2

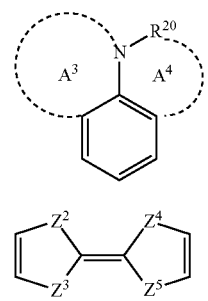

General Formula 3

Wherein $Z^1$=H, O, S, or Si; $A^1$ and $A^2$ may independently form an aromatic ring, a aromatic heterocycle, an aliphatic or a nonaromatic heterocycle respectively; in general formula, $R^{20}$ represents H, aryl, or an atomic group necessary to form a ring represented by $A^4$, and $A^3$ and $A^4$ may also independently form aromatic heterocycle or nonaromatic heterocycle respectively; in general formula 3, $Z^2$, $Z^3$, $Z^4$, and $Z^5$ independently represent O or S respectively.

In a preferred embodiment, the electron donating group described above is selected from groups having any backbone of the following general formulas D1-D10:

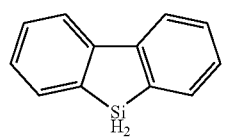

D1

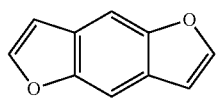

D2

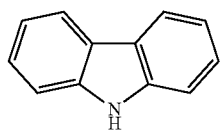

D3

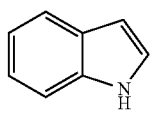

D4

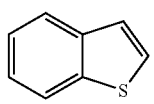

D5

D6

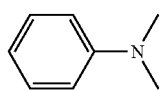

D7

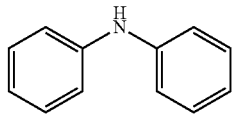

D8

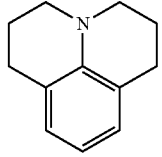

D9

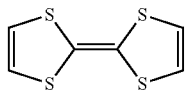

D10

The suitable electron accepting group A is selected from F, cyano group, or groups having any backbone of the following general formulas:

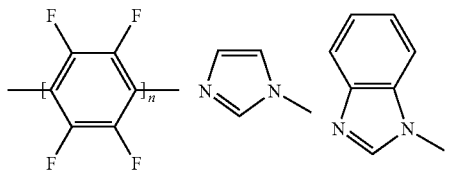
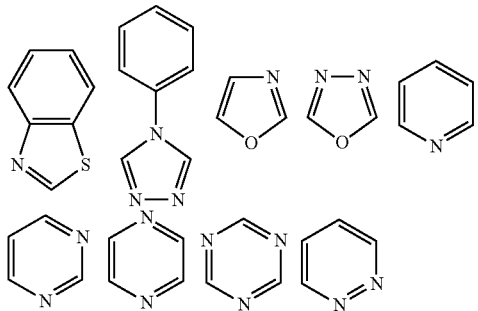
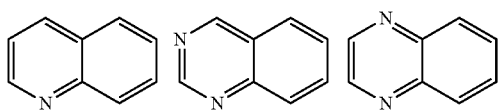
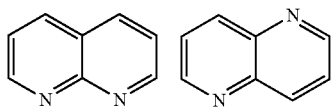
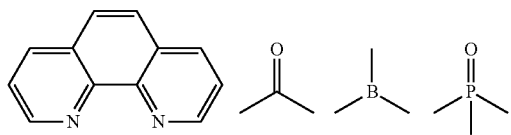
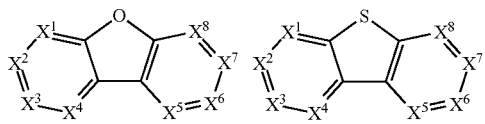

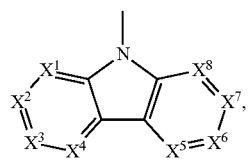

wherein n1 is an integer from 1 to 3, $X^1$-$X^8$ are $CR^1$ or N, at least one of $X^1$-$X^8$ is N, and $R^1$ is selected from the group consisting of hydrogen, alkyl, alkoxy, amino, alkene, alkyne, aralkyl, heteroalkyl, aryl, and heteroaryl.

In a preferred embodiment, the suitable electron accepting group A is selected from cyano group.

In a preferred embodiment, Ar in the repeating structural unit E of the polymer according to the present disclosure is selected from the following groups:

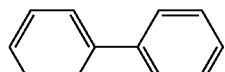

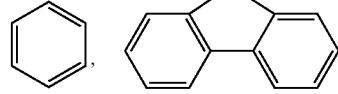

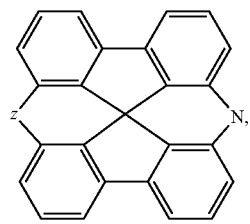

Wherein z is O or S.

Examples of suitable repeating structural unit E are listed below:

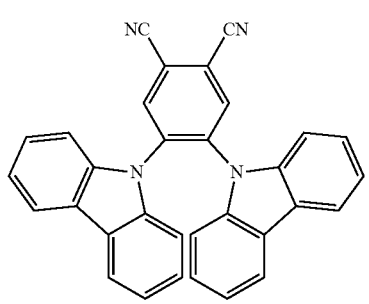
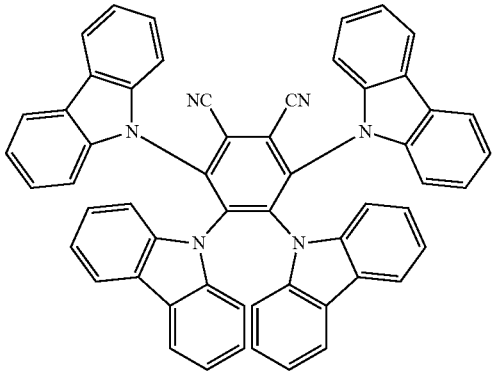

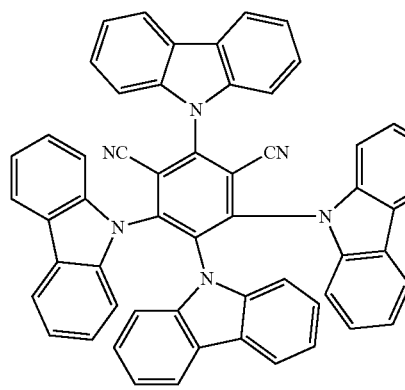
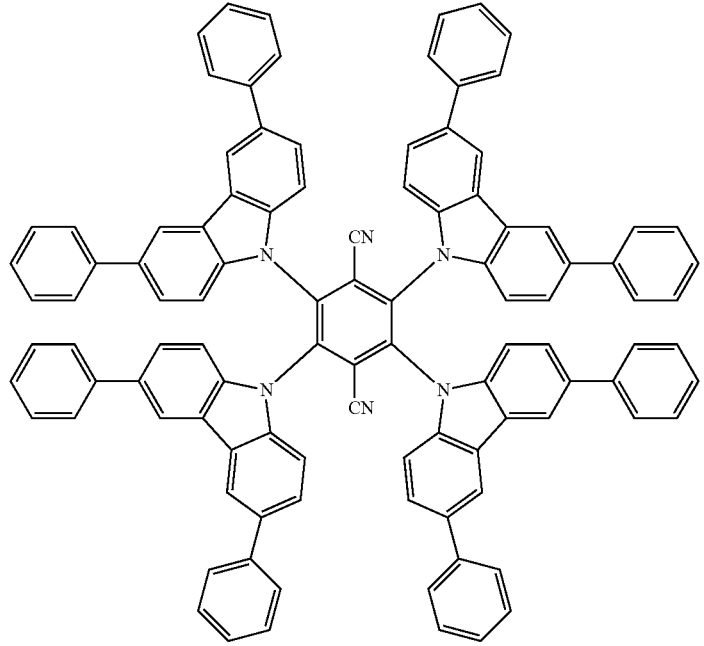
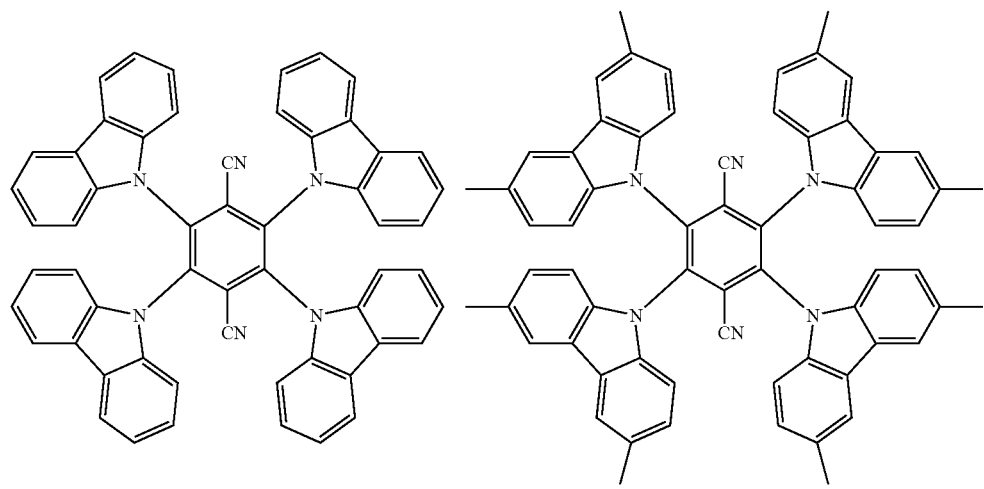
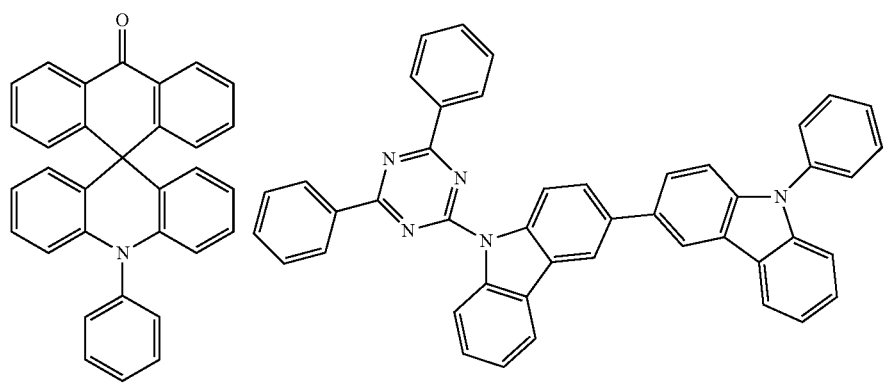

-continued
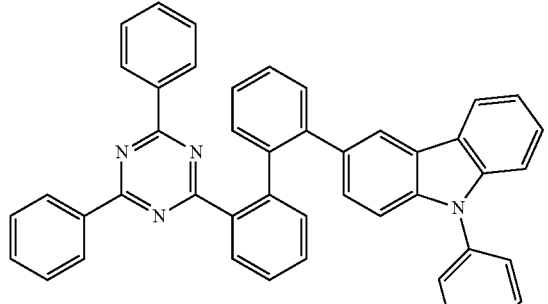
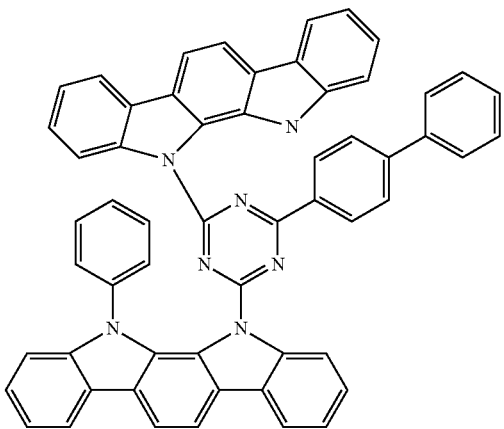
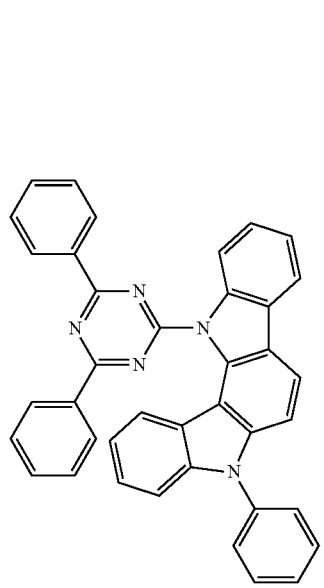
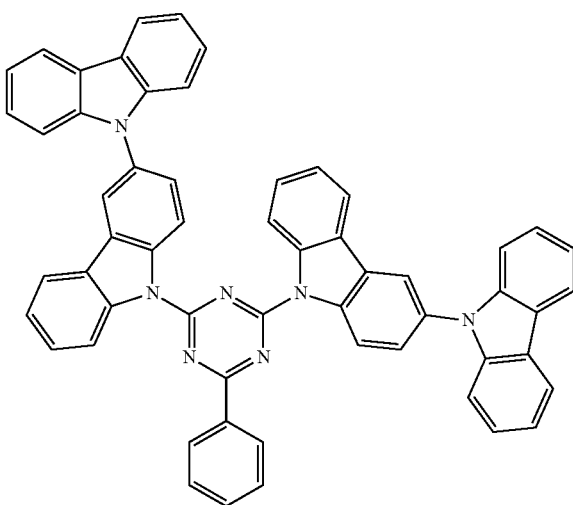
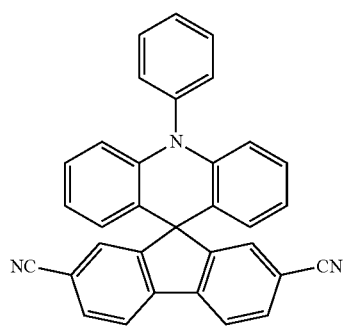
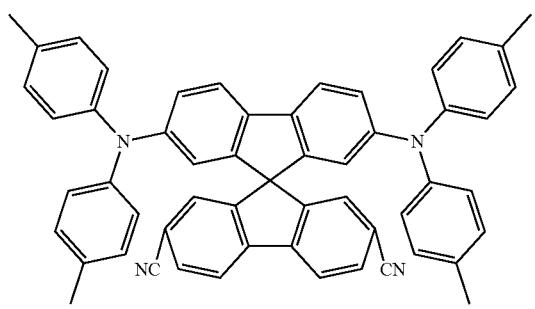

-continued
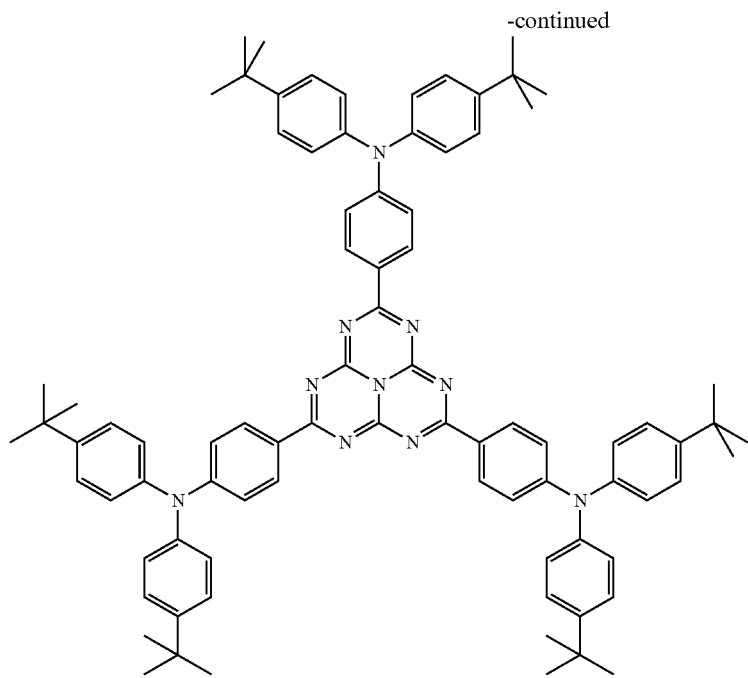
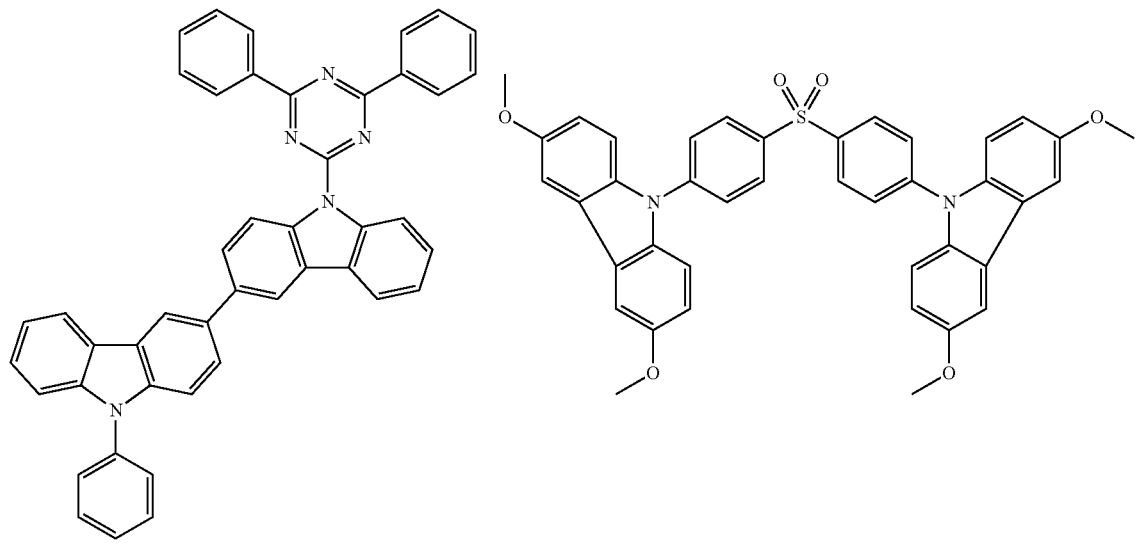
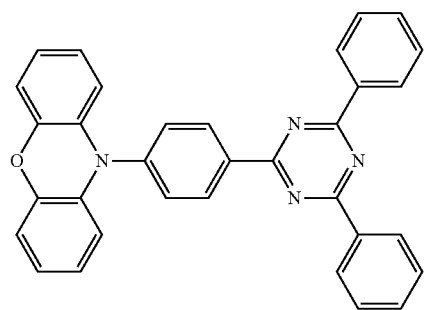 [SMILES: c1ccc(-c2nc(-c3ccccc3)nc(-c3ccc(N4c5ccccc5Oc5ccccc54)cc3)n2)cc1]

In the present disclosure, the repeating structural unit E may be independently of each other selected from the same or different structural groups in multiple occurrences.

In a preferred embodiment, the polymer according to the present disclosure further contains an organic functional group.

In some embodiments, the polymer according to the present disclosure has the following general formulas:

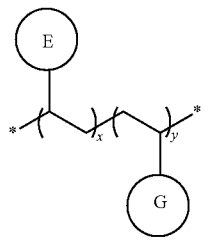

Wherein G is the organic functional group, x, y are the molar fractions, and x+y=1.

The organic functional group G may be the same or different in multiple occurances and independently selected from a hole (also called an electron hole)-injecting or hole-transporting group, a hole-blocking group, an electron-injecting or electron-transporting group, an electron-blocking group, an organic host group, a singlet emitter group (fluorescent emitter group), and a triplet emitter group (phosphorescent emitter group) in multiple occurrences. These organic functional groups corresponds to small molecules of organic functional materials: a hole (also called an electron hole)-injecting or hole-transporting material (HIM/HTM), a hole-blocking material (HBM), an electron-injecting or electron-transporting material (EIM/ETM), an electron-blocking material (EBM), an organic host material (Host), a singlet emitter (fluorescent emitter), and a triplet emitter (phosphorescent emitter). These organic functional materials are described in detail, for example, in WO2010135519A1, US20090134784A1, and WO 2011110277A1. The three patent documents are specially incorporated herein by reference in their entirety.

The following is a more detailed description the organic functional material (but not limited thereto).

1. HIM/HTM

Suitable organic HIM/HTM materials may be selected from the compounds containing the following structural units: phthalocyanines, porphyrins, amines, aryl amines, biphenyl triaryl amines, thiophenes, thiophenes such as dithiophenethiophene and thiophthene, pyrrole, aniline, carbazole, indeno-fluorene, and derivatives thereof.

Examples of cyclic aromatic amine-derived compounds that may be used as HTM or HIM include, but are not limited to, the general structure as follows:

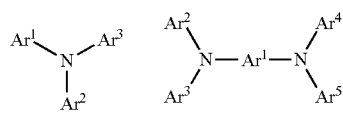

-continued

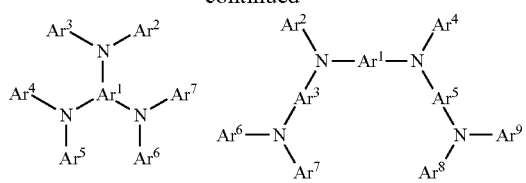

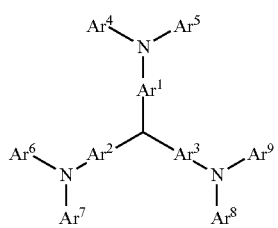

Each of $Ar^1$-$Ar^9$ is independently selected from cyclic aromatic hydrocarbon compounds, such as benzene, biphenyl, triphenyl, benzo, naphthalene, anthracene, phenalene, phenanthrene, fluorene, pyrene, chrysene, perylene, azulene; heterocyclic aryl compounds, such as triphenylamine, dibenzothiophene, dibenzofuran, furan, thiophene, benzofuran, benzothiophene, carbazole, pyrazole, imidazole, triazole, isoxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, dibenzoselenophene, benzoselenophene, benzofuropyridine, indolocarbazole, pyridylindole, pyrrolodipyridine, furodipyridine, benzothienopyridine, thienodipyridine, benzoselenophenopyridine and selenophenodipyridine; and groups comprising 2 to 10 ring structures, which may be the same or different types of cyclic aryl or heterocyclic aryl and are linked to each other directly or by at least one of the following groups, such as oxygen atom, nitrogen atom, sulfur atom, silicon atom, phosphorus atom, boron atom, chain structure unit, and aliphatic rings, wherein each Ar may be further substituted and the substituents may be selected from hydrogen, alkyl, alkoxy, amino, alkene, alkyne, aralkyl, heteroalkyl, aryl and heteroaryl.

In one aspect, $Ar^1$ to $Ar^9$ may be independently selected from the following groups:

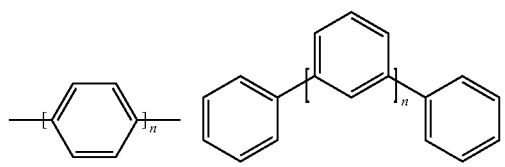

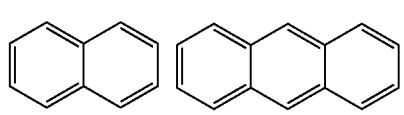

-continued

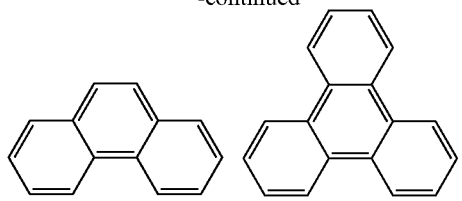

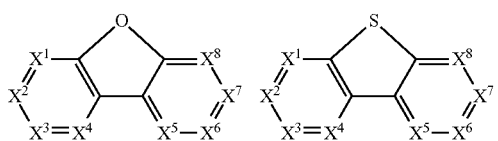

wherein n is an integer from 1 to 20; $X^1$-$X^8$ are CH or N; $Ar^1$ is defined as above. Additional examples of cyclic aromatic amine-derived compounds may be found in U.S. Pat. Nos. 3,567,450, 4,720,432, 5,061,569, 3,615,404, and 5,061,569.

Examples of metal complexes that may be used as HTM or HIM include, but are not limited to, the general structure as follows:

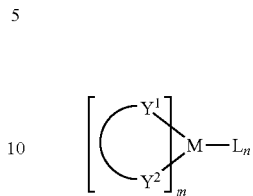

M is metal having an atomic weight greater than 40;

($Y^1$-$Y^2$) is a bidentate ligand, wherein $Y^1$ and $Y^2$ are independently selected from C, N, O, P, and S; L is an auxiliary ligand; m is an integer from 1 to the maximum coordination number of the metal; m+n is the maximum coordination number of the metal.

In one embodiment, ($Y^1$-$Y^2$) is a 2-phenylpyridine derivative.

In another embodiment, ($Y^1$-$Y^2$) is a carbene ligand.

In another embodiment, M is selected from Ir, Pt, Os, and Zn.

In another aspect, the HOMO of the metal complex is greater than −5.5 eV (relative to the vacuum level).

Examples of suitable HIM/HTM compounds are listed in the following table:

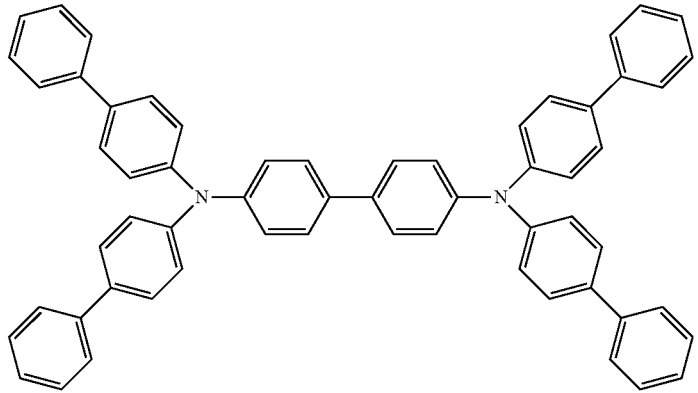

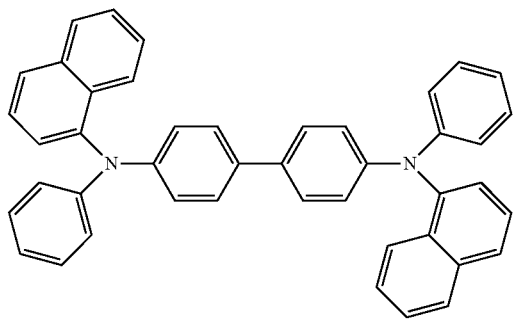

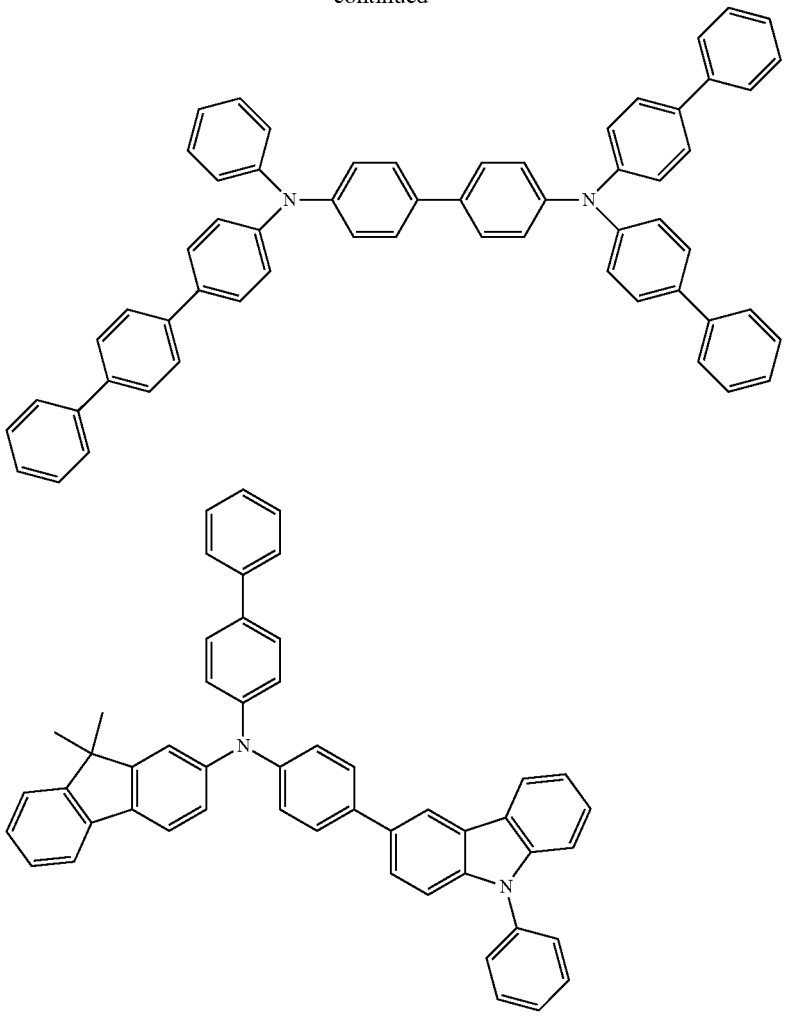

2. EIM/ETM/HBM

Examples of EIM/ETM material are not particularly limited, and any metal complex or organic compound may be used as EIM/ETM as long as they can transfer electrons. Preferred organic EIM/ETM materials may be selected from the group consisting of tris (8-quinolinolato) aluminum (AlQ3), phenazine, phenanthroline, anthracene, phenanthrene, fluorene, bifluorene, spiro-bifluorene, phenylene-vinylene, triazine, triazole, imidazole, pyrene, perylene, trans-indenofluorene, cis-indenonfluorene, dibenzol-indenofluorene, indenonaphthalene, benzanthracene and their derivatives.

The hole-blocking layer (HBL) is typically used to block holes from adjacent functional layers, particularly light-emitting layers. In contrast to a light-emitting device without a barrier layer, the presence of HBL usually leads to an increase in luminous efficiency. The hole-blocking material (HBM) of the hole-blocking layer (HBL) requires a lower HOMO than the adjacent functional layer, such as the light-emitting layer. In a preferred embodiment, the HBM has a greater energy level of excited state than the adjacent light-emitting layer, such as a singlet or triplet, depending on the emitter. In another preferred embodiment, the HBM has an electron-transport function. Typically, EIM/ETM materials with deep HOMO levels may be used as HBM.

In another aspect, compounds that may be used as EIM/ETM/HBM compounds may be molecules comprising at least one of the following groups:

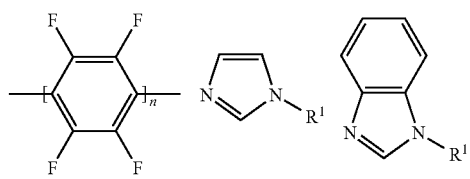

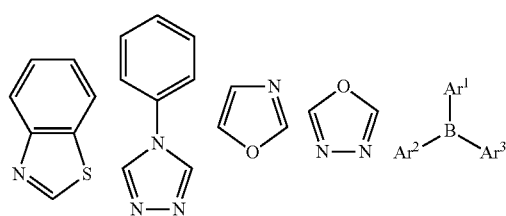

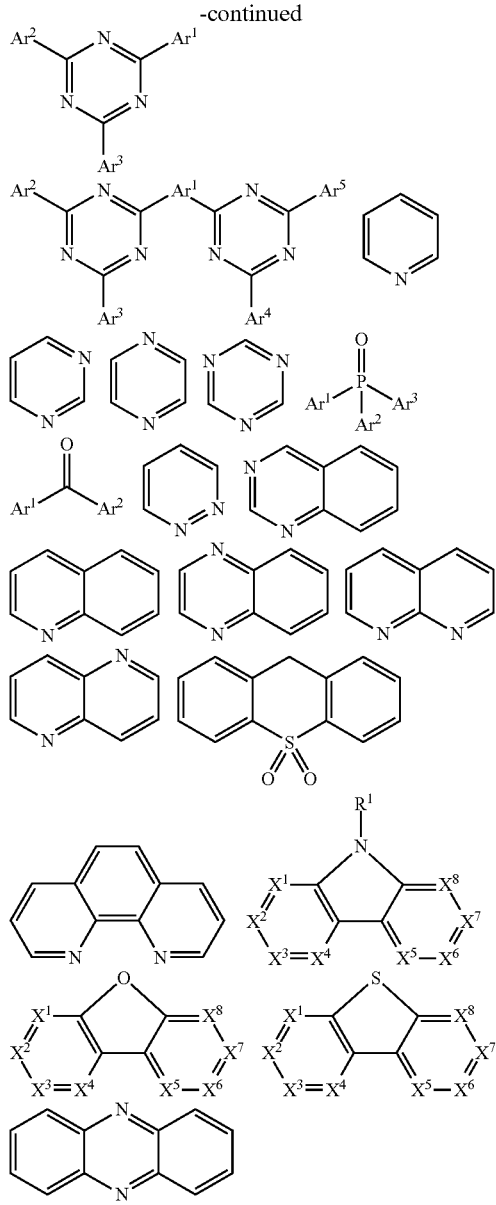

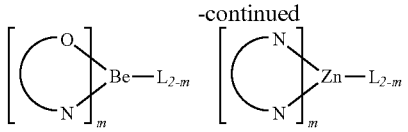

O—N) or (N—N) is a bidentate ligand, wherein the metal coordinates with O, N, or N, N; L is an auxiliary ligand; and m is an integer whose value is from 1 to the maximum coordination number of the metal.

Examples of suitable ETM compounds are listed in the following table:

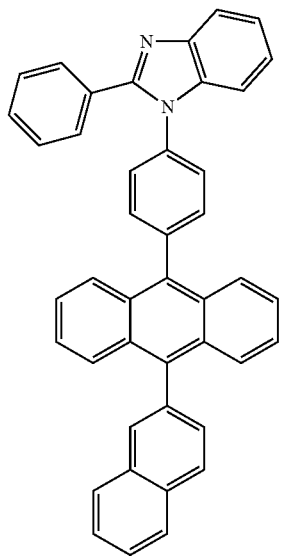

R$^1$ is selected from the following groups: hydrogen, alkyl, alkoxy, amino, alkene, alkyne, aralkyl, heteroalkyl, aryl and heteroaryl, which have the same meaning as Ar$^1$ and Ar$^2$ in HTM as described above when they are aryl or heteroaryl;

Ar$^1$-Ar$^5$ has the same meaning as Ar$^1$ in HTM as described above;

n is an integer from 0 to 20;

X$^1$-X$^8$ are selected from CR$^1$ or N.

On the other hand, examples of metal complexes that may be used as EIM/ETM include, but are not limited to, the following general structure:

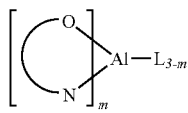 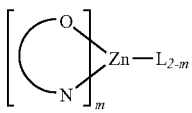

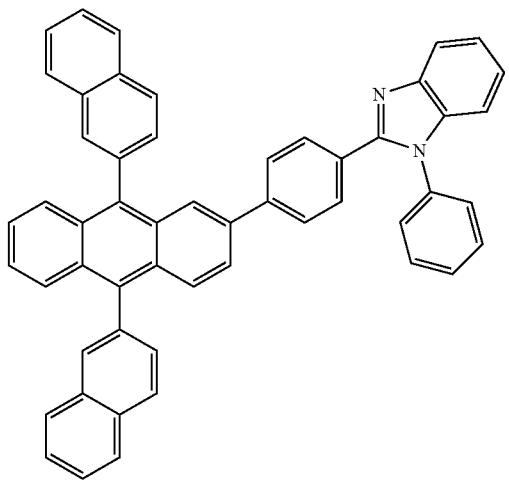

-continued

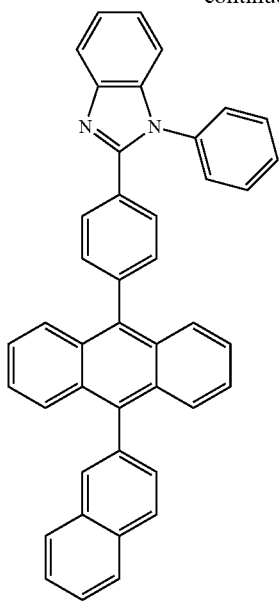

In another preferred embodiment, the organic alkali metal compound may be used as the EIM. In the present disclosure, the organic alkali metal compound may be understood as a compound having at least one alkali metal, i.e., lithium, sodium, potassium, rubidium, and cesium, and further comprising at least one organic ligand.

Suitable organic alkali metal compounds include the compounds described in U.S. Pat. No. 7,767,317 B2, EP 1941562B1 and EP 1144543B1.

The preferred organic alkali metal compound are a compound of the following formula:

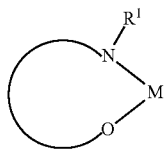

wherein $R^1$ has the same meaning as described above, and the arc represents two or three atoms and the bond to form a 5- or 6-membered ring with metal M when necessary, while the atoms may be substituted with one or more $R^1$; and wherein M is an alkali metal selected from lithium, sodium, potassium, rubidium, and cesium.

The organic alkali metal compound may be in the form of a monomer, as described above, or in the form of an aggregate, for example, two alkali metal ions with two ligands, 4 alkali metal ions and 4 ligands, 6 alkali metal ions and 6 ligand, or in other forms.

The preferred organic alkali metal compound is a compound of the following formula:

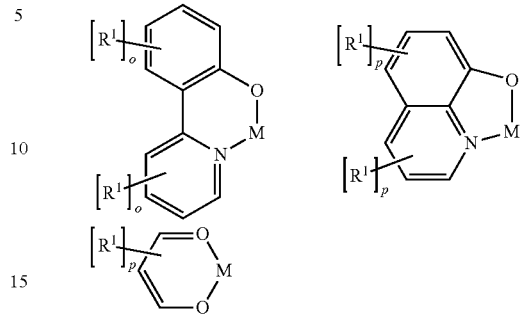

Wherein the symbols used are as defined above, and in addition:

o, each time it may be the same or different, selected from 0, 1, 2, 3 or 4; and p, each time it may be the same or different, selected from 0, 1, 2 or 3.

In a preferred embodiment, the alkali metal M is selected from the group consisting of lithium, sodium, potassium, more preferably lithium or sodium, and most preferably lithium.

In a preferred embodiment, the organic alkali metal compound is used in the electron-injection layer, and more preferably the electron-injection layer consists of the organic alkali metal compound.

In another preferred embodiment, the organic alkali metal compound is doped into other ETMs to form an electron-transport layer or an electron-injection layer, more preferably an electron-transport layer.

Examples of suitable organic alkali metal compounds are listed in the following table:

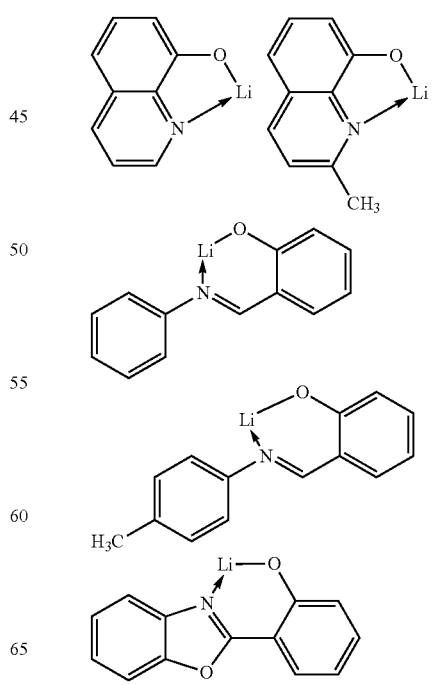

-continued

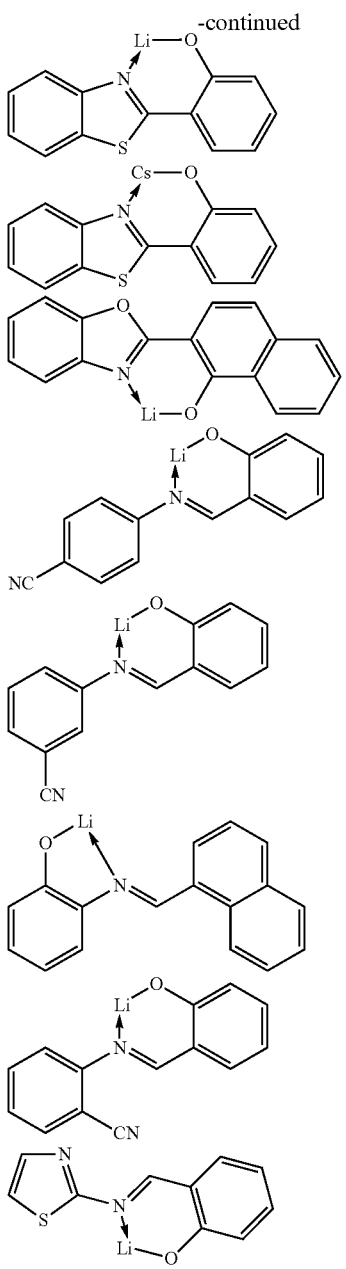

3. Triplet Host Materials:

Examples of a triplet host material are not particularly limited and any metal complex or organic compound may be used as the host material as long as its triplet energy is greater than that of the light emitter, especially a triplet emitter or phosphorescent emitter.

Examples of metal complexes that may be used as triplet hosts may include, but are not limited to, the general structure as follows:

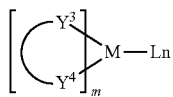

wherein M is a metal; $(Y^3-Y^4)$ is a bidentate ligand, $Y^3$ and $Y^4$ are independently selected from C, N, O, P, and S; L is an auxiliary ligand; m is an integer with the value from 1 to the maximum coordination number of the metal; and, m+n is the maximum number of coordination of the metal.

In a preferred embodiment, the metal complex which may be used as the triplet host has the following form:

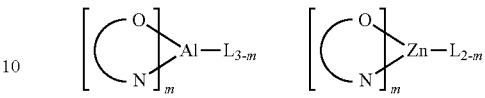

(O—N) is a bidentate ligand in which the metal is coordinated to O and N atoms.

In one embodiment, M may be selected from Ir and Pt.

Examples of organic compounds that may be used as triplet host are selected from: compounds containing cyclic aryl groups, such as benzene, biphenyl, triphenyl, benzo, and fluorene; compounds containing heterocyclic aryl groups, such as triphenylamine, dibenzothiophene, dibenzofuran, dibenzoselenophen, furan, thiophene, benzofuran, benzothiophene, benzoselenophene, carbazole, indolocarbazole, indolopyridine, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, or a combination thereof; and groups containing 2 to 10 ring structures, which may be the same or different types of cyclic aryl or heterocyclic aryl and are linked to each other directly or by at least one of the following groups, such as oxygen atom, nitrogen atom, sulfur atom, silicon atom, phosphorus atom, boron atom, chain structure unit, and aliphatic ring, wherein each Ar may be further substituted and the substituents may be selected from hydrogen, alkyl, alkoxy, amino, alkene, alkyne, aralkyl, heteroalkyl, aryl and heteroaryl.

In a preferred embodiment, the triplet host materials are selected from compounds comprising at least one of the following groups:

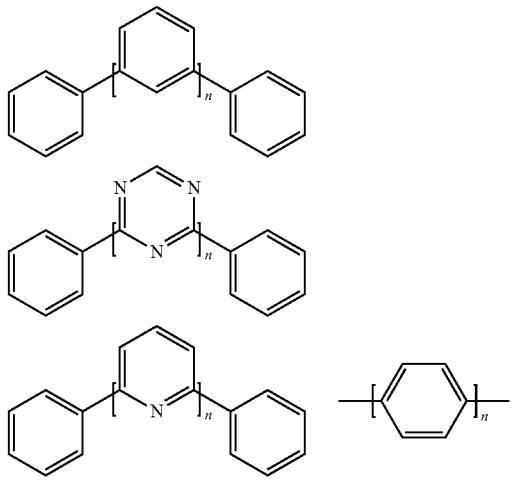

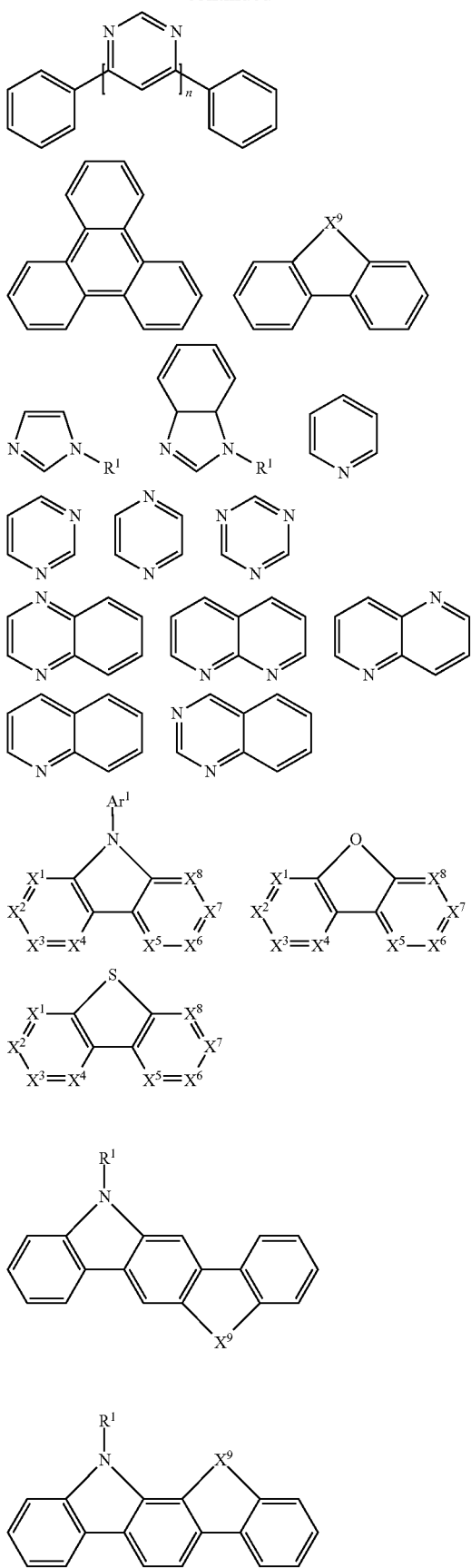
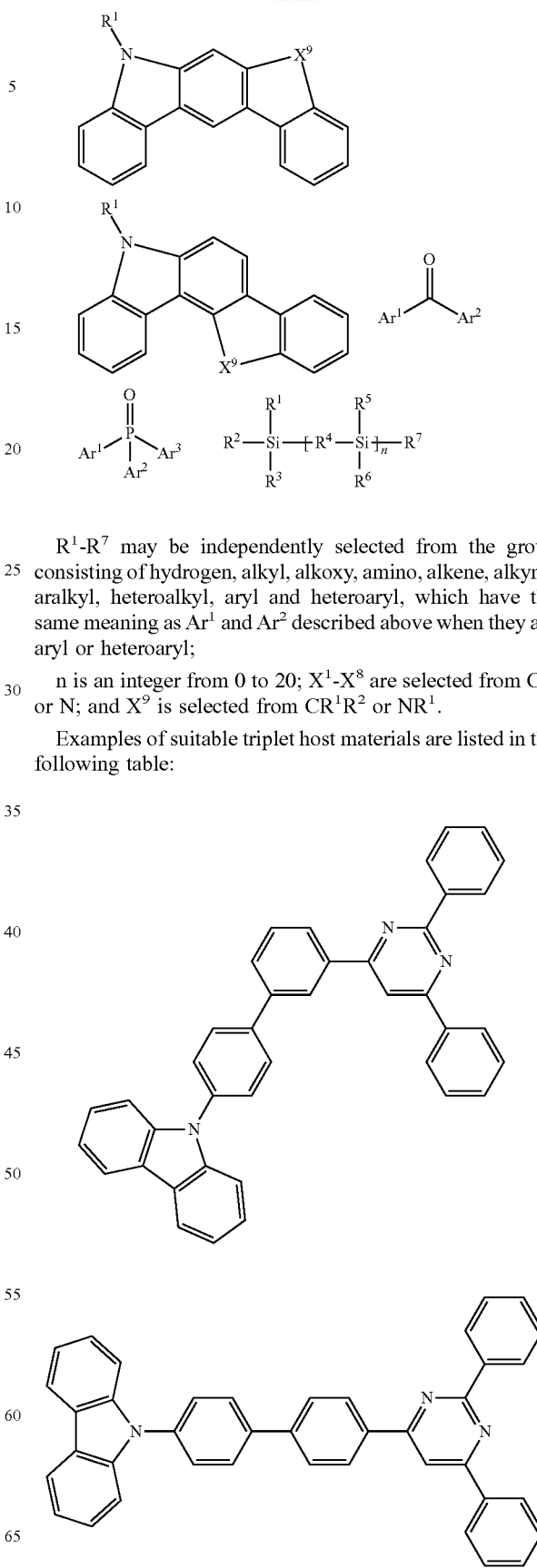

$R^1$-$R^7$ may be independently selected from the group consisting of hydrogen, alkyl, alkoxy, amino, alkene, alkyne, aralkyl, heteroalkyl, aryl and heteroaryl, which have the same meaning as $Ar^1$ and $Ar^2$ described above when they are aryl or heteroaryl;

n is an integer from 0 to 20; $X^1$-$X^8$ are selected from CH or N; and $X^9$ is selected from $CR^1R^2$ or $NR^1$.

Examples of suitable triplet host materials are listed in the following table:

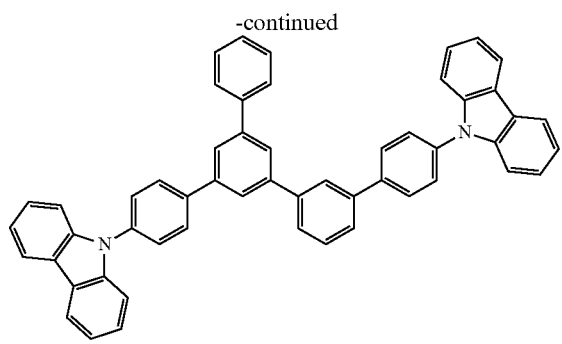

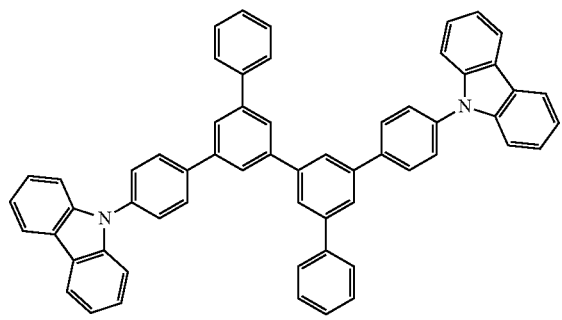

4. Singlet Host Material:

Examples of singlet host material are not particularly limited and any organic compound may be used as the host as long as its singlet state energy is greater than that of the light emitter, especially the singlet emitter or fluorescent light emitter.

Examples of organic compounds used as singlet host materials may be selected from: cyclic aryl compounds, such as benzene, biphenyl, triphenyl, benzo, naphthalene, anthracene, phenalene, phenanthrene, fluorene, pyrene, chrysene, perylene, azulene; heterocyclic aryl compounds, such as triphenylamine, dibenzothiophene, dibenzofuran, dibenzoselenophen, furan, thiophene, benzofuran, benzothiophene, benzoselenophene, carbazole, indolocarbazole, indolopyridine, pyrrolodipyridine, pyrazole, imidazole, triazole, isoxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and groups comprising 2 to 10 ring structures, which may be the same or different types of cyclic aryl or heterocyclic aryl and are linked to each other directly or by at least one of the following groups, such as oxygen atom, nitrogen atom, sulfur atom, silicon atom, phosphorus atom, boron atom, chain structure unit, and aliphatic rings.

In a preferred embodiment, the singlet host material may be selected from compounds comprising at least one of the following groups:

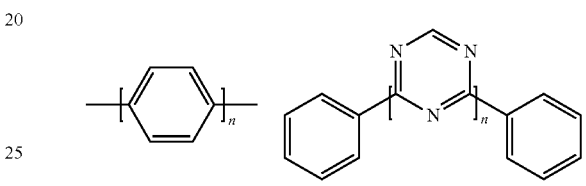

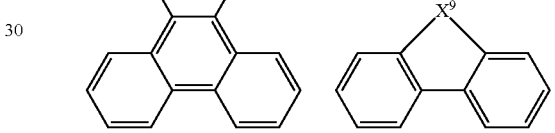

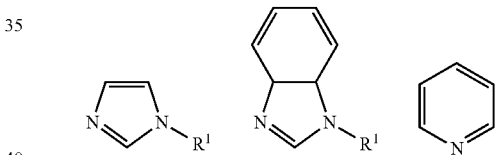

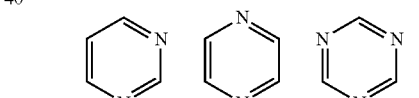

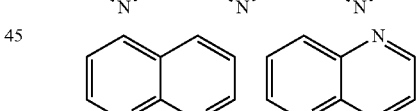

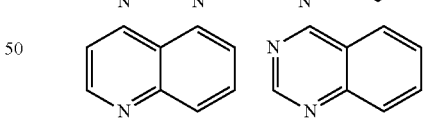

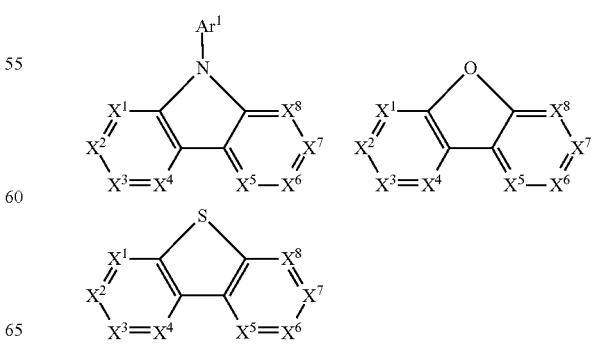

-continued

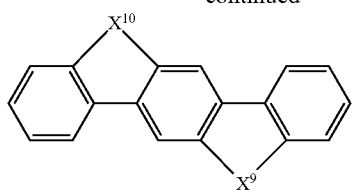

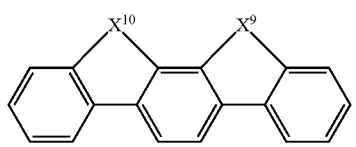

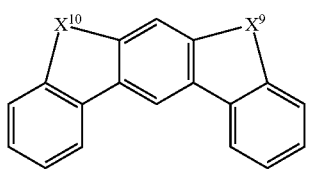

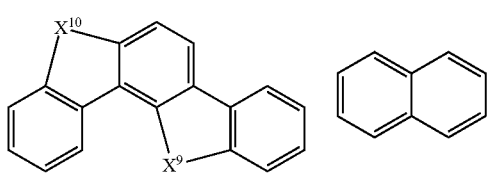

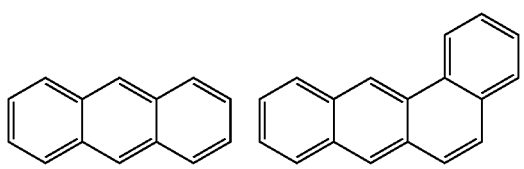

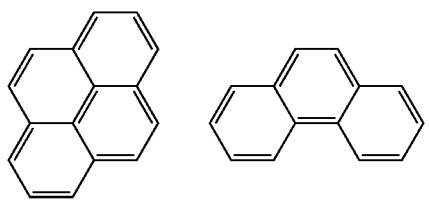

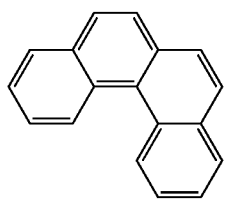

$R^1$ may be independently selected from the group consisting of hydrogen, alkyl, alkoxy, amino, alkene, alkyne, aralkyl, heteroalkyl, aryl and heteroaryl; $Ar^1$ is aryl or heteroaryl and has the same meaning as $Ar^1$ defined in the HTM above;

n is an integer from 0 to 20; $X^1$-$X^8$ is selected from CH or N; $X^9$ and $X^{10}$ are selected from $CR^1R^2$ or $NR^1$.

Examples of suitable singlet host materials are listed in the following table:

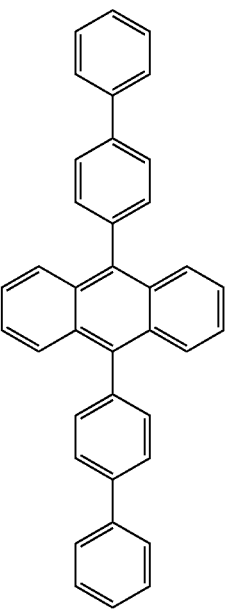
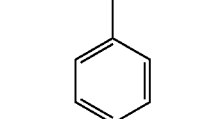
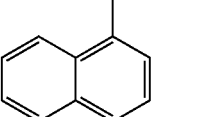
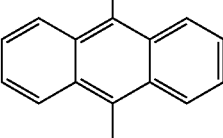

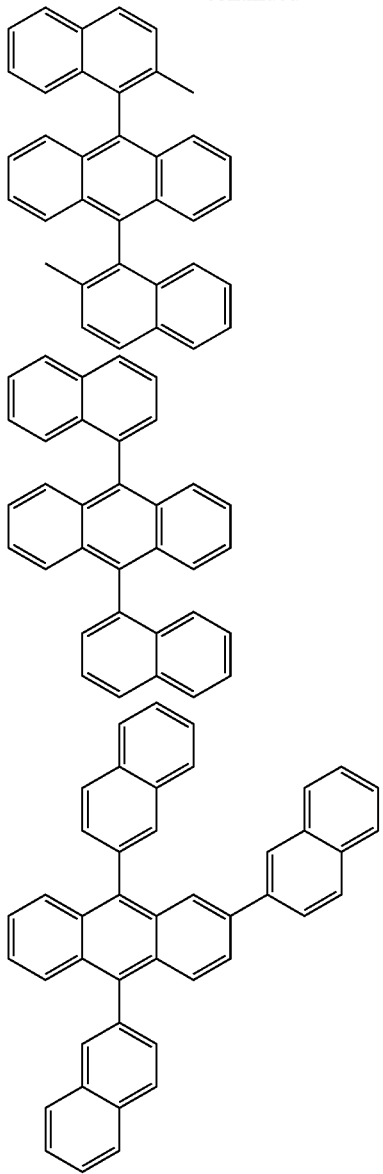

5. Singlet Emitter

The singlet emitter tends to have a longer conjugate π-electron system. To date, there have been many examples, such as styrylamine and its derivatives disclosed in JP2913116B and WO2001021729A1, and indenofluorene and its derivatives disclosed in WO2008/006449 and WO2007/140847.

In a preferred embodiment, the singlet emitter may be selected from monostyrylamines, distyrylamines, tristyrylamines, tetrastyrylamines, styrylphosphines, styryl ethers, and arylamines.

Monostyrylamine refers to a compound which comprises one unsubstituted or substituted styryl group and at least one amine, most preferably an aryl amine. Distyrylamine refers to a compound comprising two unsubstituted or substituted styryl groups and at least one amine, most preferably an aryl amine. Ternarystyrylamine refers to a compound which comprises three unsubstituted or substituted styryl groups and at least one amine, most preferably an aryl amine. Quaternarystyrylamine refers to a compound comprising four unsubstituted or substituted styryl groups and at least one amine, most preferably an aryl amine. Preferred styrene is stilbene, which may be further substituted. The corresponding phosphines and ethers are defined similarly to amines. Aryl amine or aromatic amine refers to a compound comprising three unsubstituted or substituted cyclic or heterocyclic aryl systems directly attached to nitrogen. At least one of these cyclic or heterocyclic aryl systems is preferably selected from fused ring systems and most preferably has at least 14 aryl ring atoms. Among the preferred examples are aryl anthramine, aryl anthradiamine, aryl pyrene amines, aryl pyrene diamines, aryl chrysene amines and aryl chrysene diamine. Aryl anthramine refers to a compound in which one diarylamino group is directly attached to anthracene, most preferably at position 9. Aryl anthradiamine refers to a compound in which two diarylamino groups are directly attached to anthracene, most preferably at positions 9, 10. Aryl pyrene amines, aryl pyrene diamines, aryl chrysene amines and aryl chrysene diamine are similarly defined, wherein the diarylarylamino group is most preferably attached to position 1 or 1 and 6 of pyrene.

Examples of singlet emitter based on vinylamine and arylamine are also preferred examples which may be found in the following patent documents: WO 2006/000388, WO 2006/058737, WO 2006/000389, WO 2007/065549, WO 2007/115610, U.S. Pat. No. 7,250,532 B2, DE 102005058557 A1, CN 1583691 A, JP 08053397 A, U.S. Pat. No. 6,251,531 B1, US 2006/210830 A, EP 1957606 A1, and US 2008/0113101 A1. The patent documents listed above are specially incorporated herein by reference in their entirety.

Examples of singlet light emitters based on distyrylbenzene and its derivatives may be found in, for example, U.S. Pat. No. 5,121,029.

More preferred singlet emitter may be selected from indenofluorene-amine and indenofluorene-diamine, such as those disclosed in WO 2006/122630; benzoindenofluorene-amine and benzoindenofluorene-diamine, such as those disclosed in WO 2008/006449, and dibenzoindenofluorene-amine and dibenzoindenofluorene-diamine, such as those disclosed in WO2007/140847.

Other materials useful as singlet emissors include polycyclic aryl compounds, especially one selected from the derivatives of the following compounds: anthracenes such as 9,10-di-naphthylanthracene, naphthalene, tetraphenyl, phenanthrene, perylene such as 2,5,8,11-tetra-t-butylatedylene, indenoperylene, phenylenes such as 4,4'-(bis (9-ethyl-3-carbazovinylene)-1,1'-biphenyl, periflanthene, decacyclene, coronene, fluorene, spirobifluorene, arylpyren (e.g., US20060222886), arylenevinylene (e.g., U.S. Pat. Nos. 5,121,029, 5,130,603), cyclopentadiene such as tetraphenylcyclopentadiene, rubrene, coumarine, rhodamine, quinacridone, pyrane such as 4 (dicyanoethylene)-6-(4-dimethylaminostyryl-2-methyl)-4H-pyrane (DCM), thiapyran, bis (azinyl) imine-boron compounds (US 2007/0092753 A1), bis (azinyl) methene compounds, carbostyryl compounds, oxazone, benzoxazole, benzothiazole, benzimidazole, and diketopyrrolopyrrole. Some singlet emitter materials may be found in the following patent documents: US 20070252517 A1, U.S. Pat. Nos. 4,769,292, 6,020,078, US 2007/0252517 A1, and US 2007/0252517 A1. The patent documents listed above are specially incorporated herein by reference in their entirety.

Examples of suitable singlet emitters are listed in the following table:

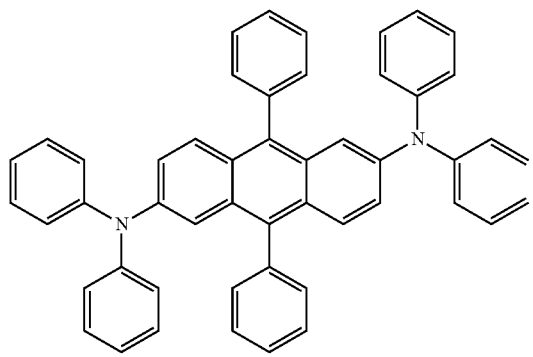

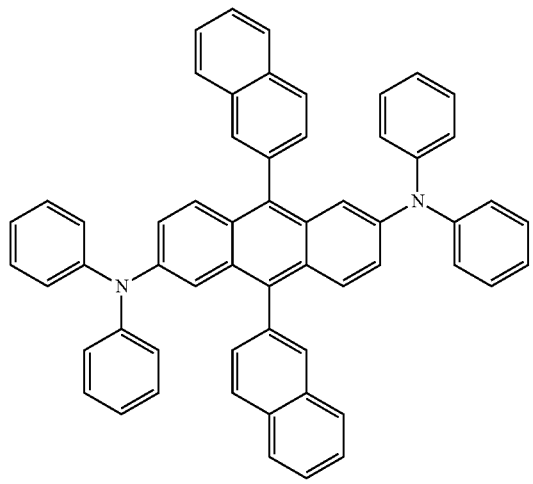

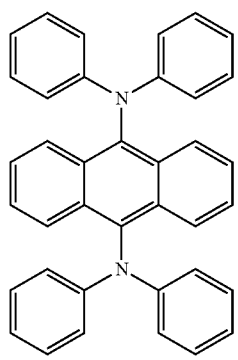

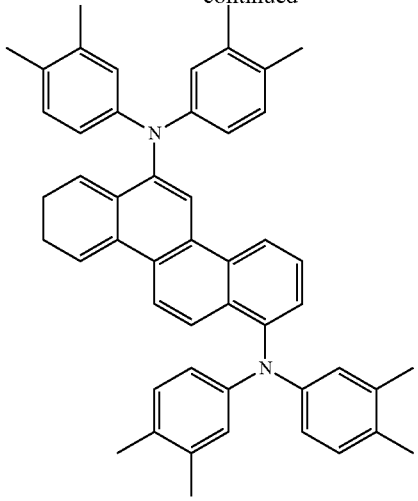

6. Triplet Emitter

The triplet emitter is also called a phosphorescent emitter. In a preferred embodiment, the triplet emitter is a metal complex of the general formula M (L) n, wherein M may be a metal atom; L may be a same or different ligand each time it is present, and may be bonded or coordinated to the metal atom M at one or more positions; n may be an integer greater than 1, preferably 1, 2, 3, 4, 5 or 6. Alternatively, these metal complexes may be attached to a polymer by one or more positions, most preferably through an organic ligand.

In a preferred embodiment, the metal atom M may be selected from the group consisting of transition metal elements or lanthanides or actinides, preferably Ir, Pt, Pd, Au, Rh, Ru, Os, Sm, Eu, Gd, Tb, Dy, Re, Cu or Ag, and particularly preferably Os, Ir, Ru, Rh, Re, Pd, or Pt.

Preferably, the triplet emitter comprises a chelating ligand, i.e., a ligand, coordinated to the metal by at least two bonding sites, and it is particularly preferred that the triplet emitter comprises two or three identical or different bidentate or multidentate ligand. Chelating ligands help to improve stability of metal complexes.

Examples of organic ligands may be selected from the group consisting of phenylpyridine derivatives, 7,8-benzoquinoline derivatives, 2 (2-thienyl) pyridine derivatives, 2 (1-naphthyl) pyridine derivatives, or 2 phenylquinoline derivatives. All of these organic ligands may be o substituted, for example, substituted with fluoromethyl or trifluoromethyl. The auxiliary ligand may be preferably selected from acetylacetonate or picric acid.

In a preferred embodiment, the metal complex which may be used as the triplet emitter has the following form:

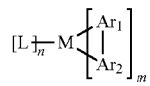

wherein M is a metal selected from the group consisting of transition metal elements or lanthanides or actinides; $Ar^1$ may be the same or different cyclic group each time it is present, which comprises at least one donor atom, that is, an atom with a lone pair of electrons, such as nitrogen atom or phosphorus atom, which is coordinated to the metal through its ring group; $Ar^2$ may be the same or different cyclic group comprising at least one C atom each time it is present and is coordinated to the metal through its ring group; $Ar^1$ and $Ar^2$ are covalently bonded together, wherein each of them may carry one or more substituents which may also be joined together by substituents; L may be the same or different at each occurrence and is an auxiliary ligand, preferably a bidentate chelating ligand, and most preferably a monoanionic bidentate chelating ligand; m is 1, 2 or 3, preferably 2 or 3, and particularly preferably 3; and, N is 0, 1, or 2, preferably 0 or 1, particularly preferably 0.

Examples of triplet emitter materials and their application may be found in the following patent documents and references: WO 200070655, WO 200141512, WO 200202714, WO 200215645, EP 1191613, EP 1191612, EP 1191614, WO 2005033244, WO 2005019373, US 2005/0258742, WO 2009146770, WO 2010015307, WO 2010031485, WO 2010054731, WO 2010054728, WO 2010086089, WO 2010099852, WO 2010102709, US 20070087219 A1, US 20090061681 A1, US 20010053462 A1, Baldo, Thompson et al. Nature 403, (2000), 750-753, US 20090061681 A1, US 20090061681 A1, Adachi et al. Appl. Phys. Lett. 78 (2001), 1622-1624, J. Kido et al. Appl. Phys. Lett. 65 (1994), 2124, Kido et al. Chem. Lett. 657, 1990, US 2007/0252517 A1, Johnson et al., JACS 105, 1983, 1795, Wrighton, JACS 96, 1974, 998, Ma et al., Synth. Metals 94, 1998, 245, U.S. Pat. Nos. 6,824,895, 7,029,766, 6,835,469, 6,830,828, US 20010053462 A1, WO 2007095118 A1, US 2012004407A1, WO 2012007088A1, WO2012007087A1, WO 2012007086A1, US 2008027220A1, WO 2011157339A1, CN 102282150A, WO 2009118087A1. The patent documents and references listed above are specially incorporated herein by reference in their entirety.

In a preferred embodiment, the polymer according to the present disclosure contains the aforementioned E and an organic functional group, wherein G is selected from the triplet host groups.

In another preferred embodiment, the polymer according to the present disclosure contains the aforementioned E and an organic functional group, wherein G is selected from the triplet emitter groups.

In another preferred embodiment, the polymer according to the present disclosure contains the aforementioned E and two additional organic functional groups G1 and G2, wherein G1 is selected from the triplet host groups and G2 is selected from the triplet emitter groups.

In another preferred embodiment, the polymer according to the present disclosure contains the aforementioned E and two additional organic functional groups G1 and G2, wherein G1 is selected from the hole-transporting groups and G2 is selected from the electron-transporting groups.

The present disclosure further provides a polymerizable monomer having the following general formula:

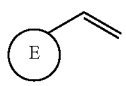

wherein for the energy difference between the singlet energy level and the triplet energy level of the structural unit E, $(S1(E)-T1(E))\leq 0.35$ eV.

In a preferred embodiment, the polymerizable monomer is provided, wherein $(S1(E)-T1(E))\leq 0.25$ eV, preferably $\leq 0.20$ eV, most preferably $\leq 0.10$ eV.

In a preferred embodiment, the structural unit E of the polymer according to the present disclosure is a structural unit containing at least one electron donating group D and at least one electron accepting group A.

In a more preferred embodiment, the structural unit E of the polymer according to the present disclosure is a structural unit having the following structural formula (II):

(II)

Wherein Ar is an aromatic or heteroaromatic structural unit, D is an electron donating group, A is an electron accepting group, n and m are an integer between 1 and 6 respectively; wherein when m>1, each D is independently of each other selected from the same or different electron donating groups, and when n>1, each A is independently of each other selected from the same or different electron accepting groups.

Suitable electron donating group D may be selected from groups having any backbone of the following general formulas 1-3:

General Formula 1

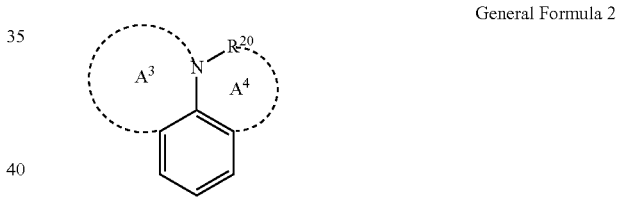

General Formula 2

General Formula 3

Wherein $Z1=H$, O, S, or Si; $A^1$ and $A^2$ may independently form an aromatic ring, a aromatic heterocycle, an aliphatic or a nonaromatic heterocycle respectively; in general formula, $R^{20}$ represents H, aryl, or an atomic group necessary to form a ring represented by $A^4$, and $A^3$ and $A^4$ may also independently form aromatic heterocycle or nonaromatic heterocycle respectively; in general formula 3, $Z^2$, $Z^3$, $Z^4$, and $Z^5$ independently represent O or S respectively.

In a preferred embodiment, the electron donating group described above is selected from groups having any backbone of the following general formulas D1-D10:

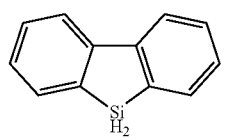

D1

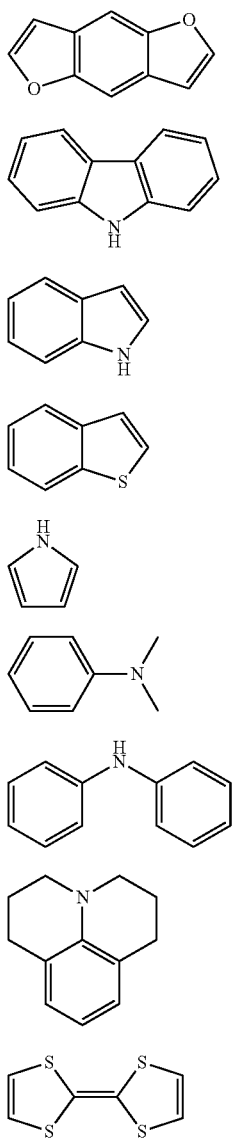

The suitable electron accepting group A is selected from F, cyano group, or groups having any backbone of the following general formulas:

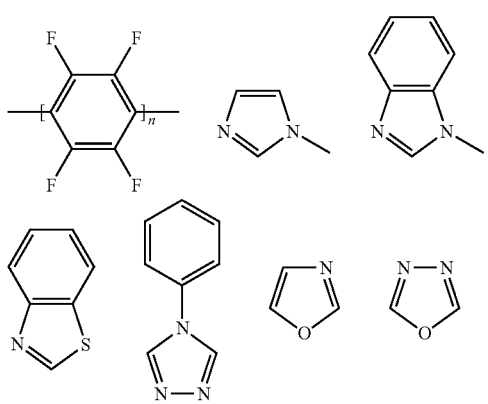

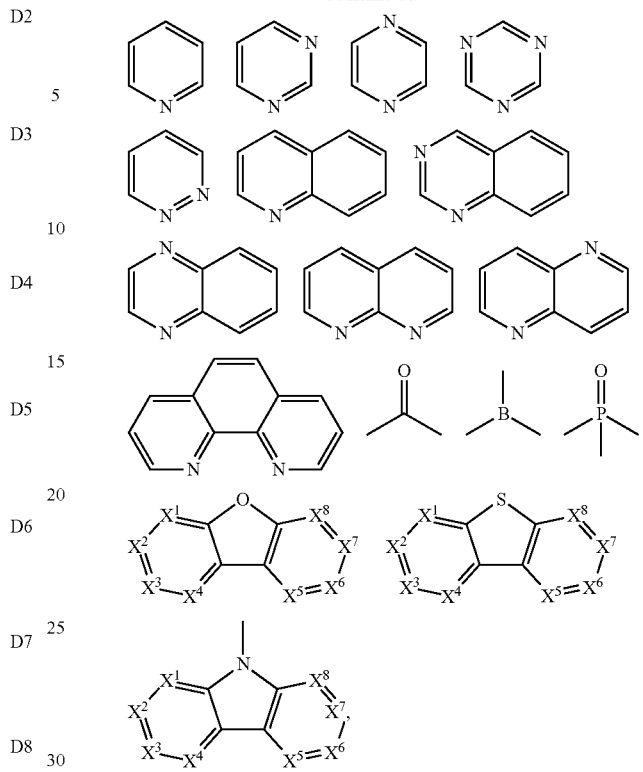

wherein n1 is an integer from 1 to 3, $X^1$-$X^8$ are $CR^1$ or N, at least one of $X^1$-$X^8$ is N, and wherein $R^1$ has the same definition as that defined as that in ETM.

In a preferred embodiment, the suitable electron accepting group A is selected from cyano group.

In a preferred embodiment, Ar in the repeating structural unit E of the polymer according to the present disclosure is selected from the following groups:

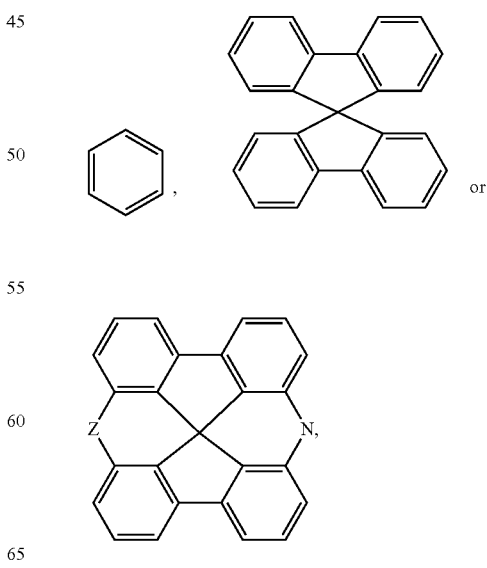

Wherein z is O or S.

Examples of suitable polymerizable monomer E are listed below:
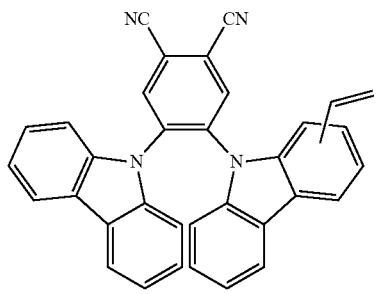
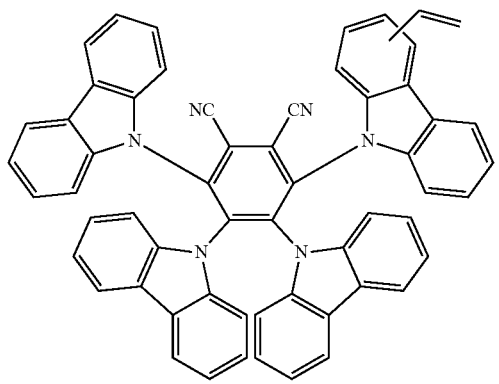
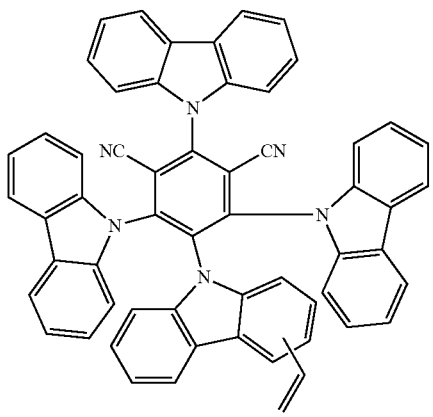
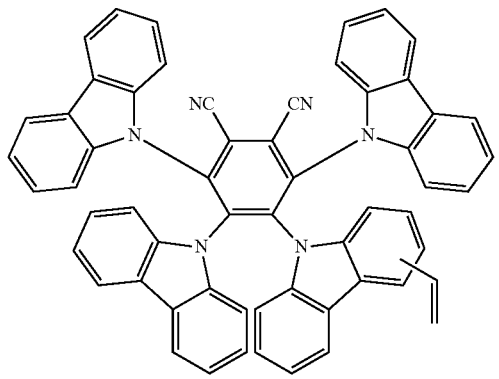
-continued
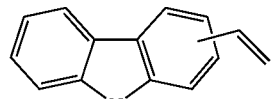
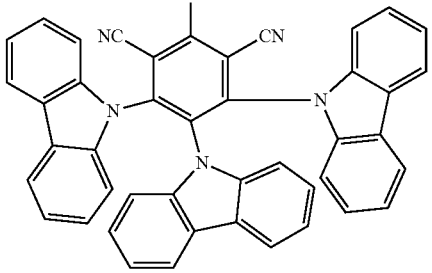
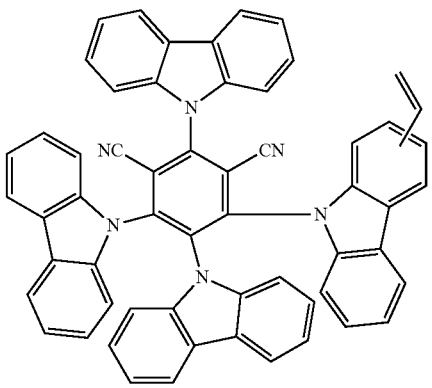
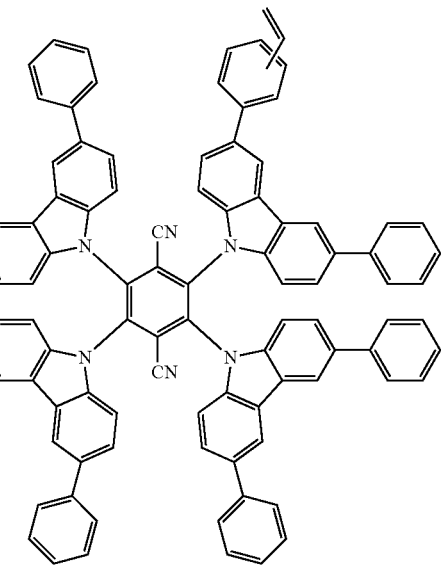

-continued
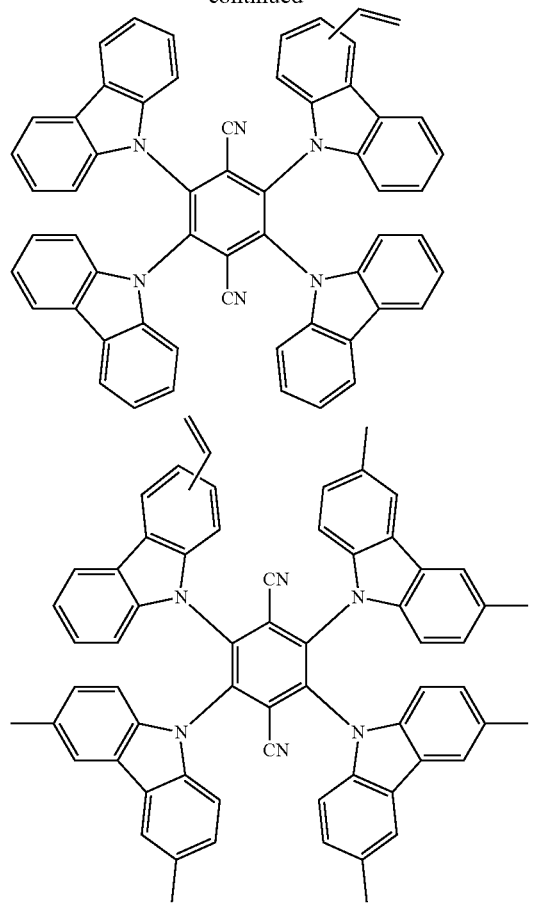
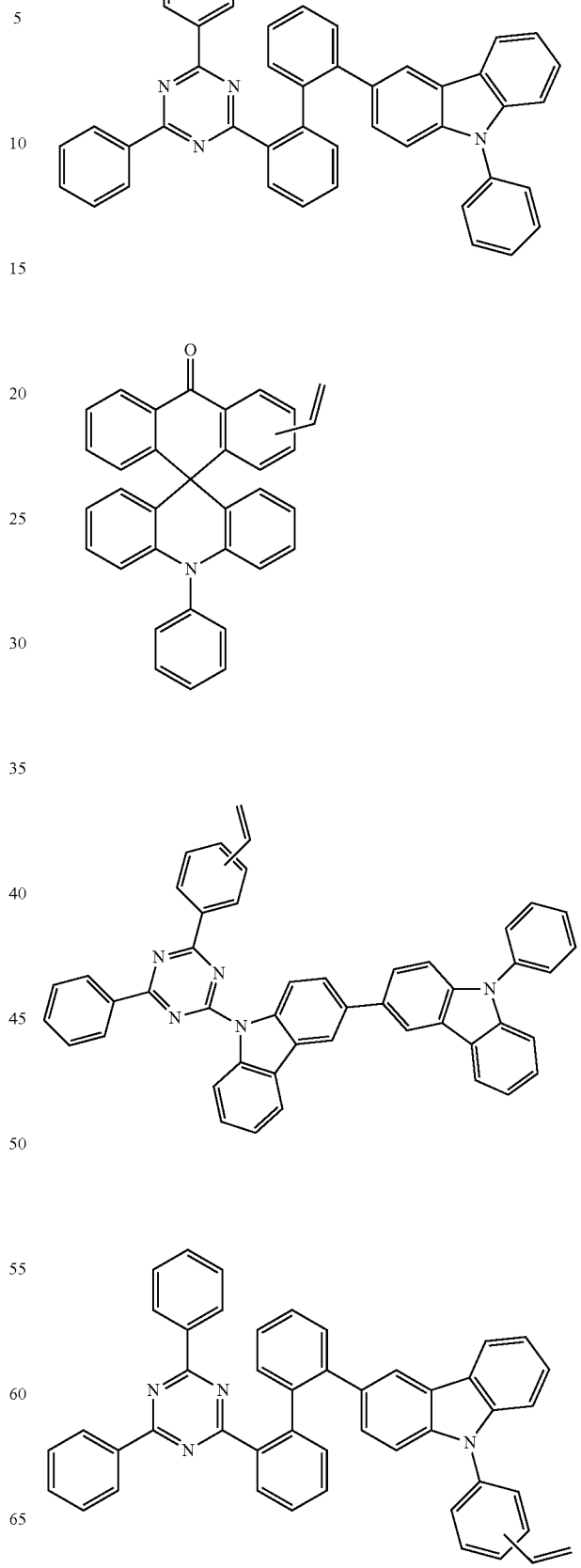

45
-continued
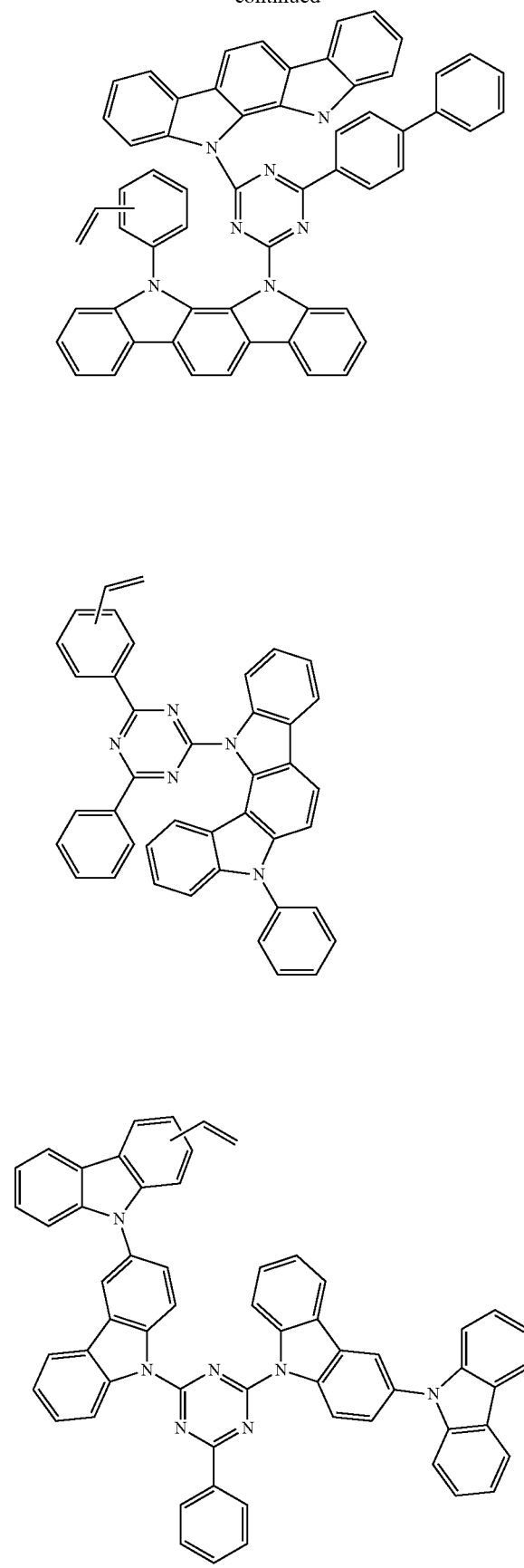
46
-continued
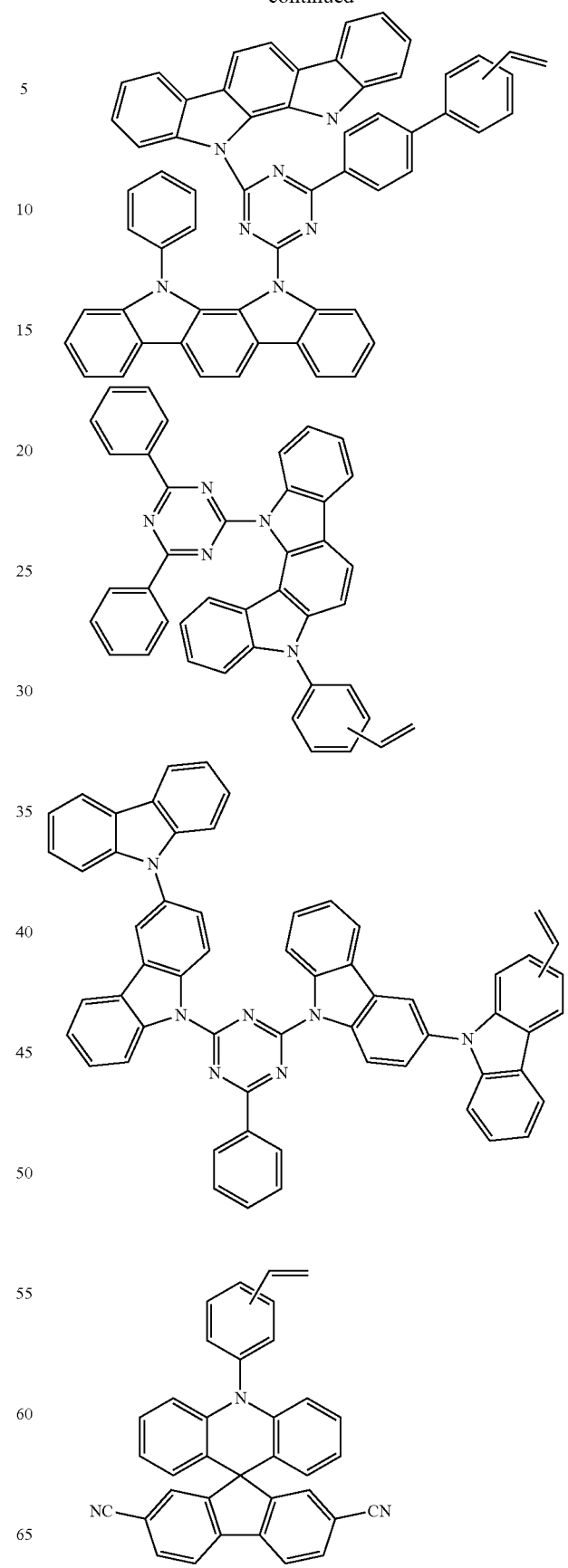

-continued

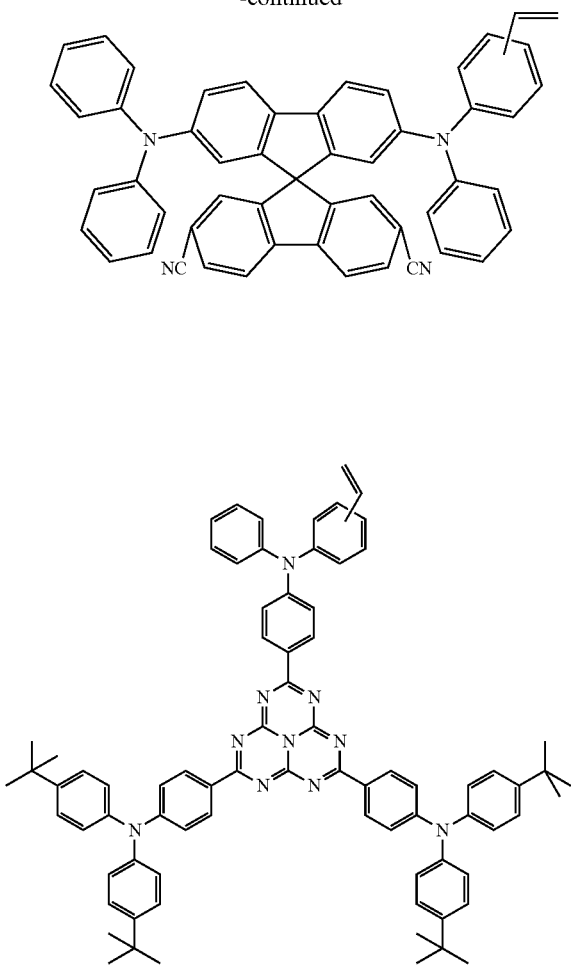

-continued

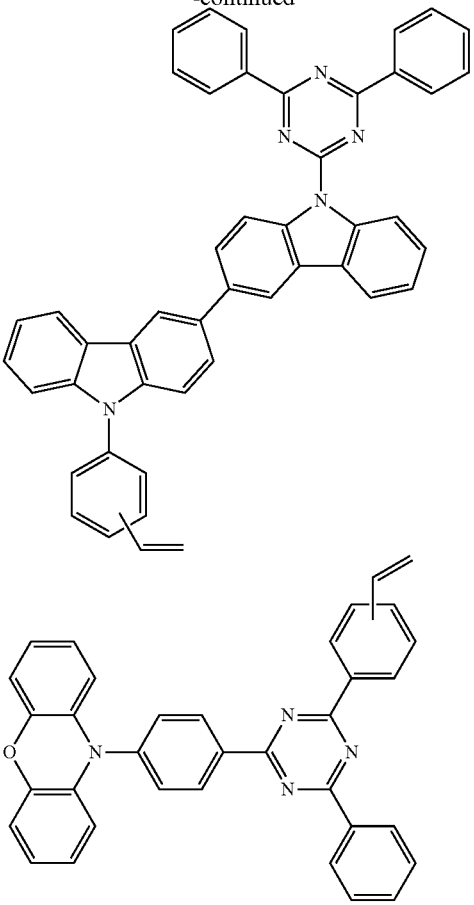

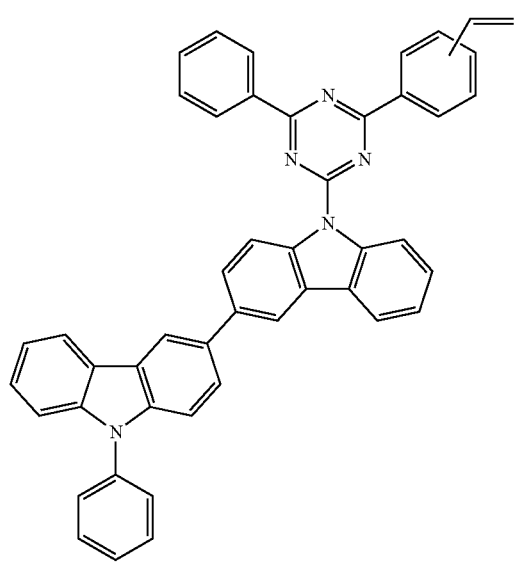

The present disclosure further provides a mixture containing at least one polymer as described above and an organic functional material selected from a hole (also called an electron hole)-injecting or hole-transporting material (HIM/HTM), a hole-blocking material (HBM), an electron-injecting or electron-transporting material (EIM/ETM), an electron-blocking material(EBM), an organic host material (Host), a singlet emitter (fluorescent emitter), and a triplet emitter (phosphorescent emitter). These functional materials are described above.

The present disclosure further relates to a formulation comprising the polymer as described above and at least one organic solvent. Examples of the organic solvents include, but are not limited to, methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxahexane, acetone, methyl ethyl ketone, 1,2-dichloroethane, 3-phenoxytoluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, naphthane, indene and/or their combination.

In a preferred embodiment, the formulation according to the present disclosure is a solution.

In another preferred embodiment, the formulation according to the present disclosure is a suspension.

The formulation in the examples of the present disclosure may comprise the polymer from 0.01 to 20 wt %, more preferably from 0.1 to 15 wt %, more preferably from 0.2 to 10 wt %, and most preferably from 0.25 to 5 wt %.

The present disclosure also provides the use of said formulation as a coating or printing ink in the preparation of organic electronic devices, and particularly preferably by means of printing or coating in a preparation process.

Among them, suitable printing or coating techniques may include, but are not limited to, ink-jet printing, typography, screen printing, dip coating, spin coating, blade coating, roll printing, torsion printing, lithography, flexography, rotary printing, spray coating, brush coating or pad printing, slit type extrusion coating, and so on. Preferred are gravure printing, screen printing and inkjet printing. The solution or suspension may additionally comprise one or more components such as surface active compounds, lubricants, wetting agents, dispersing agents, hydrophobic agents, binders, etc., for adjusting viscosity, film forming properties, improving adhesion, and the like. For more information about printing techniques and their requirements for solutions, such as solvent, concentration, viscosity, etc., see Handbook of Print Media: Technologies and Production Methods, edited by Helmut Kipphan, ISBN 3-540-67326-1.

Based on the above polymer, the present disclosure also provides the application of the polymer as described above, i,e. the application of the polymer to an organic electronic device, which may be selected from, but not limited to, organic light emitting diodes (OLED), organic photovoltaics (OPVs), organic light emitting cells (OLEEC), organic field effect transistor (OFET), organic light emitting field effectors, organic lasers, organic spin electron devices, organic sensors, and organic plasmon emitting diodes, especially OLED. In the embodiments of the present disclosure, the organic compound is preferably used in the light-emitting layer of the OLED device.

In a preferred embodiment, the polymer is used in the light-emitting layer of the OLED device.

The present disclosure further provides an organic electronic device which comprises at least one polymer as described above. Typically, such an organic electronic device comprises at least a cathode, an anode, and a functional layer between the cathode and the anode, wherein the functional layer comprises at least one of the polymers as described above. The organic electronic device may be selected from, but not limited to, organic light emitting diodes (OLED), organic photovoltaics (OPVs), organic light emitting cells (OLEEC), organic field effect transistor (OFET), organic light emitting field effectors, organic lasers, organic spin electron devices, organic sensors, and organic plasmon emitting diodes In a particularly preferred embodiment, the above-described organic electronic device is OLED, which may include a substrate, an anode, at least one light-emitting layer, and a cathode.

The substrate may be opaque or transparent. Transparent substrates may be used to make transparent light-emitting components. See, for example, Bulovic et al., Nature 1996, 380, p 29, and Gu et al., Appl. Phys. Lett. 1996, 68, p 2606. The substrate may be rigid or flexible. The substrate may be plastic, metal, semiconductor wafer or glass. Most preferably the substrate has a smooth surface. Substrates free of surface defects are particularly desirable. In a preferred embodiment, the substrate is flexible and may be selected from polymer films or plastic, with a glass transition temperature (Tg) of 150° C. or above, more preferably above 200° C., more preferably above 250° C., and most preferably above 300° C. Examples of suitable flexible substrates are poly (ethylene terephthalate) (PET) and polyethylene glycol (2,6-naphthalene) (PEN).

The anode may comprise a conductive metal or a metal oxide, or a conductive polymer. The anode may easily inject holes into the hole-injection layer (HIL) or the hole-transport layer (HTL) or the light-emitting layer. In one embodiment, the absolute value of the difference between the work function of the anode and the HOMO energy level or the valence band energy level of the emitter in the light-emitting layer or of the p-type semiconductor material of the HIL or HTL or the electron-blocking layer (EBL) is smaller than 0.5 eV, more preferably smaller than 0.3 eV, and most preferably smaller than 0.2 eV. Examples of anode materials include, but are not limited to, Al, Cu, Au, Ag, Mg, Fe, Co, Ni, Mn, Pd, Pt, ITO, aluminum-doped zinc oxide (AZO), and the like. Other suitable anode materials are known and may be readily selected for use by one of ordinary skill in the art. The anode material may be deposited using any suitable technique, such as suitable physical vapor deposition, including RF magnetron sputtering, vacuum thermal evaporation, electron beam (e-beam), and the like. In some embodiments, the anode is patterned. The patterned ITO conductive substrate is commercially available and may be used to fabricate the device according to the disclosure.

The cathode may comprise a conductive metal or a metal oxide. The cathode may easily inject electrons into the EIL or ETL or directly into the light-emitting layer. In one embodiment, the absolute value of the difference between the work function of the cathode and the LUMO energy level or the valence band energy level of the emitter in the light-emitting layer or of the n-type semiconductor material of the electron-injection layer (EIL) or the electron-transport layer (ETL) or the hole-blocking layer (HBL) is smaller than 0.5 eV, more preferably smaller than 0.3 eV, and most preferably smaller than 0.2 eV. In principle, all of the material that may be used as the cathode of an OLED may serve as a cathode material for the device of the present disclosure. Examples of the cathode material may include, but are not limited to, Al, Au, Ag, Ca, Ba, Mg, LiF/Al, MgAg alloys, BaF2/Al, Cu, Fe, Co, Ni, Mn, Pd, Pt, ITO. The cathode material may be deposited using any suitable technique, such as suitable physical vapor deposition, including RF magnetron sputtering, vacuum thermal evaporation, electron beam (e-beam), and the like.

OLEDs may also comprise other functional layers such as hole-injection layer (HIL), hole-transport layer (HTL), electron-blocking layer (EBL), electron-injection layer (EIL), electron-transport layer (ETL), and hole-blocking layer (HBL). Materials suitable for use in these functional layers are described in WO2010135519A1, US20090134784A1 and WO2011110277A1 in detail above. The three patent documents are specially incorporated herein by reference in their entirety.

In a preferred embodiment, in the light emitting device according to the present disclosure, the light-emitting layer thereof is prepared by printing with the formulation of the present disclosure.

The light emitting device according to the present disclosure may have a light emission wavelength between 300 and 1000 nm, preferably between 350 and 900 nm, and more preferably between 400 and 800 nm.

The present disclosure also relates to the use of the organic electronic device according to the present disclosure in a variety of electronic devices including, but not limited to, display devices, lighting devices, light sources, sensors, and the like.

The present disclosure also relates to an electronic device comprising the organic electronic device according to the present disclosure including, but not limited to, display devices, lighting devices, light sources, sensors, and the like.

The disclosure will now be described with reference to the preferred embodiments, but the disclosure is not to be construed as being limited to the following examples. It is to be understood that the appended claims are intended to cover the scope of the disclosure. Those skilled in the art will understand that modifications can be made to various embodiments of the disclosure with the teaching of the present disclosure, which will be covered by the spirit and scope of the claims of the disclosure.

EXAMPLES

Synthesis of Monomers

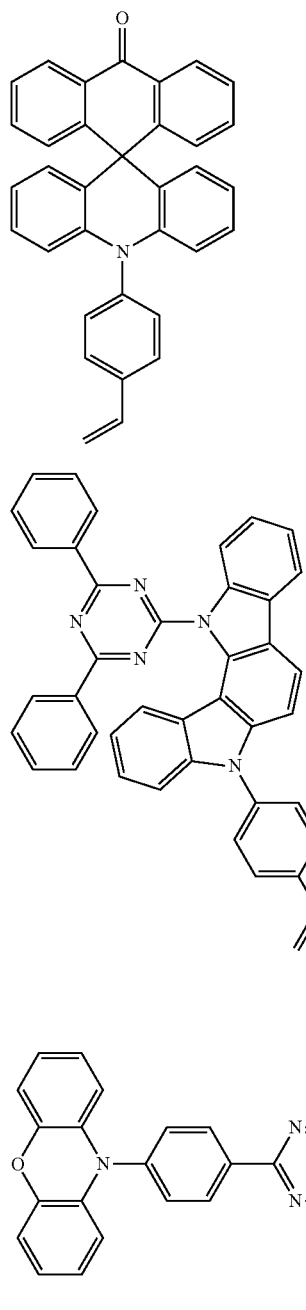

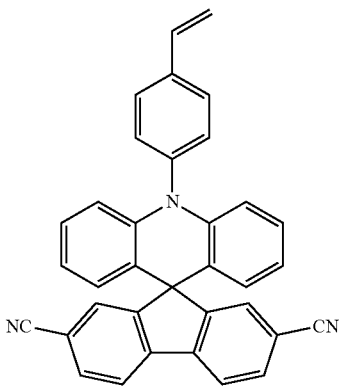

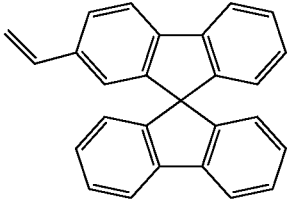

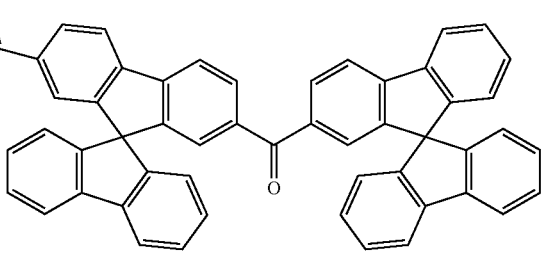

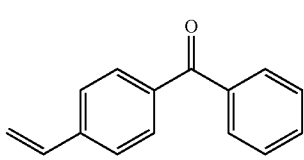

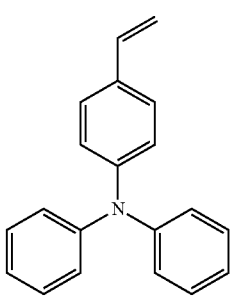

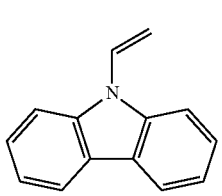

(1) Synthesis of Monomer E1

An experimental synthetic route is shown as below:

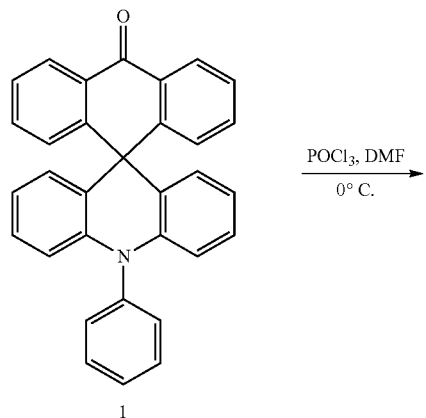

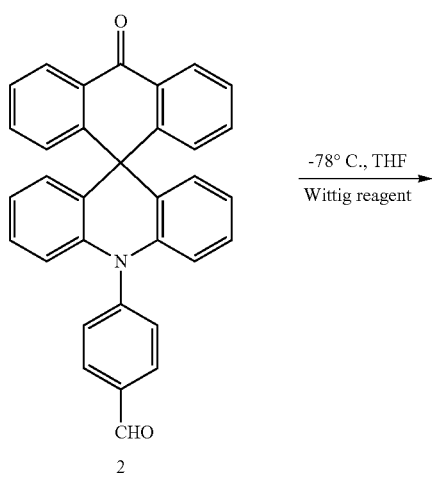

Synthesis steps are as follows:

a. 10 mmol of compound 1 was dissolved in 250 ml of dry DMF solution under the protection of a nitrogen atmosphere, the resulting reaction solution was placed in an ice bath and stirred, and 11.0 mmol of phosphorus oxychloride (POCl$_3$) solution was added dropwise. After the dropwise addition, the reaction was continued for 30 minutes, allowed to gradually warm up to room temperature and reacted for 2 hours. The reaction was quenched with water, extracted with dichloromethane, and washed with water. The organic phase was combined, dried over anhydrous sodium sulfate, filtered and the organic solvent was distilled off to give a crude product of compound 2. The crude product was recrystallized from dichloromethane and n-hexane to give 8 mmol of a product, which was dried under vacuum for use. MS(APCI)=464.4.

b. 5.0 mmol of the compound 2 obtained above was dissolved in 200 ml of dry tetrahydrofuran (THF) solution. The reaction solution was place at a temperature of −78° C. and stirred under the protection of a nitrogen atmosphere, and 8.0 mmol of methylene triphenyl phosphorane (Wittig reagent) was added dropwise. After the addition, the reaction solution was allowed to gradually warm up to room temperature and continued to stir overnight at room temperature. The reaction was quenched with water. All the reaction solution was extracted with dichloromethane, and the organic phase was washed with water. Finally, the organic phase was combined, dried over anhydrous sodium sulfate, filtered and the organic solvent was distilled off. The resulting product was purified by silica gel column with mobile phase being dichloromethane: petroleum ether=1: 2, to finally give 4.1 mmol of monomer E1, which was dried under vacuum for use. MS(APCI)=462.4.

(2) Synthesis of Monomer E2

An experimental synthetic route is shown as below:

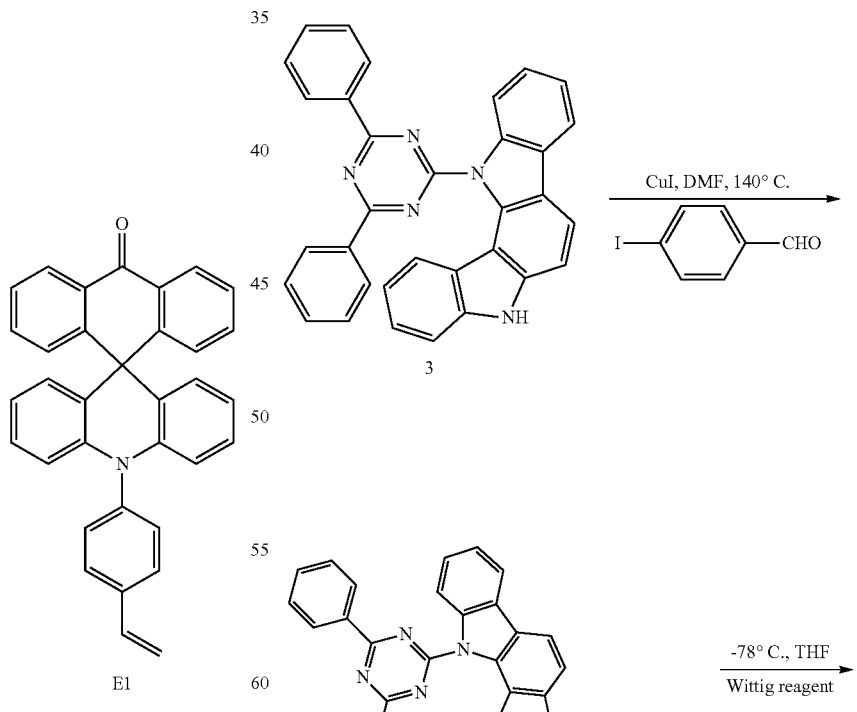

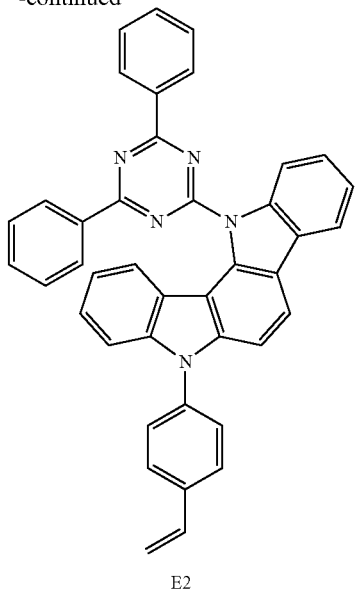

E2

Synthesis steps are as follows:

a. 1.0 mmol of compound 3, 1.2 mmol of 4-iodobenzaldehyde, 0.08 mmol of cuprous iodide, 10 mmol of potassium carbonate, 0.10 mmol of 18-crown-6 ether were added successively into a 250 ml two-necked flask in a nitrogen atmosphere, and 150 ml DMF was added to make them completely dissolved. The reaction solution was heated to 140° C. and reacted for 24 hours. The reaction solution was added with dichloromethane for dissolution when the temperature of the reaction solution was cooled to room temperature, and washed with water. Finally the organic phase was combined, dried with anhydrous sodium sulfate, filtered, and the organic solvent therein was distilled off under a reduced pressure to give a crude product 4. The crude product was recrystallized from dichloromethane and n-hexane to give 0.6 mmol of a solid powder 4, which was dried under vacuum for use. MS (APCI)=592.1.

b. 5.0 mmol of the compound 4 obtained above was dissolved in 200 ml of dry tetrahydrofuran (THF) solution. The reaction solution was placed at a temperature of −78° C. and stirred under the protection of a nitrogen atmosphere, and 8.0 mmol of methylene triphenyl phosphorane (Wittig reagent) was added dropwise. After the addition, the reaction solution was allowed to gradually warm up to room temperature and continued to stir overnight at room temperature. The reaction was quenched with water. All the reaction solution was extracted with dichloromethane, and the organic phase was washed with water. Finally, the organic phase was combined, dried over anhydrous sodium sulfate, filtered and the organic solvent was distilled off. The resulting product was purified by silica gel column with mobile phase being dichloromethane: petroleum ether=2:1, to finally give 4.5 mmol of monomer E3, which was dried under vacuum for use. MS(APCI)=590.7.

(3) Synthesis of Monomer E3

An experimental synthetic route is shown as below:

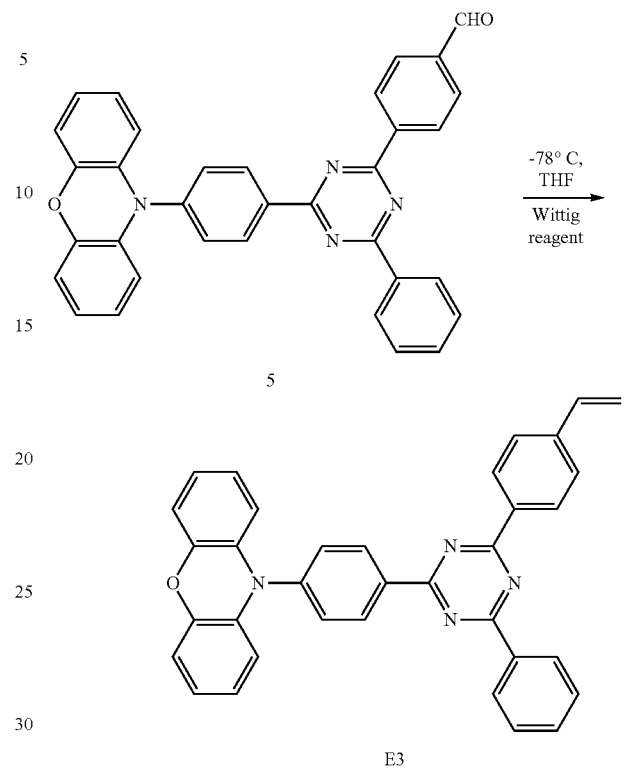

E3

Synthesis steps are as follows:

5.0 mmol of the compound 5 was dissolved in 200 ml of dry tetrahydrofuran (THF) solution. The reaction solution was placed at a temperature of −78° C. and stirred under the protection of a nitrogen atmosphere and 8.0 mmol of methylene triphenyl phosphorane (Wittig reagent) was added dropwise. After the addition, the reaction solution was allowed to gradually warm up to room temperature and continued to stir overnight at room temperature. The reaction was quenched with water. All the reaction solution was extracted with dichloromethane, and the organic phase was washed with water. Finally, the organic phase was combined, dried over anhydrous sodium sulfate, filtered and the organic solvent was distilled off. The resulting product was purified by silica gel column with mobile phase being dichloromethane: petroleum ether=3:1, to finally give 4.5 mmol of monomer E3, which was dried under vacuum for use. MS(APCI)=517.7.

(4) Synthesis of Monomer E4

An experimental synthetic route is shown as below:

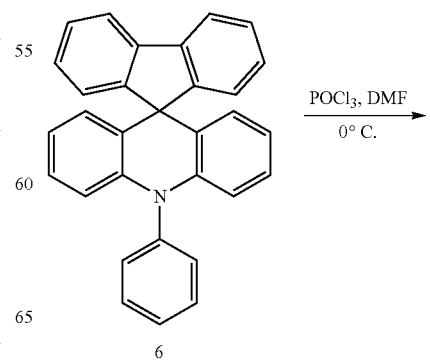

6

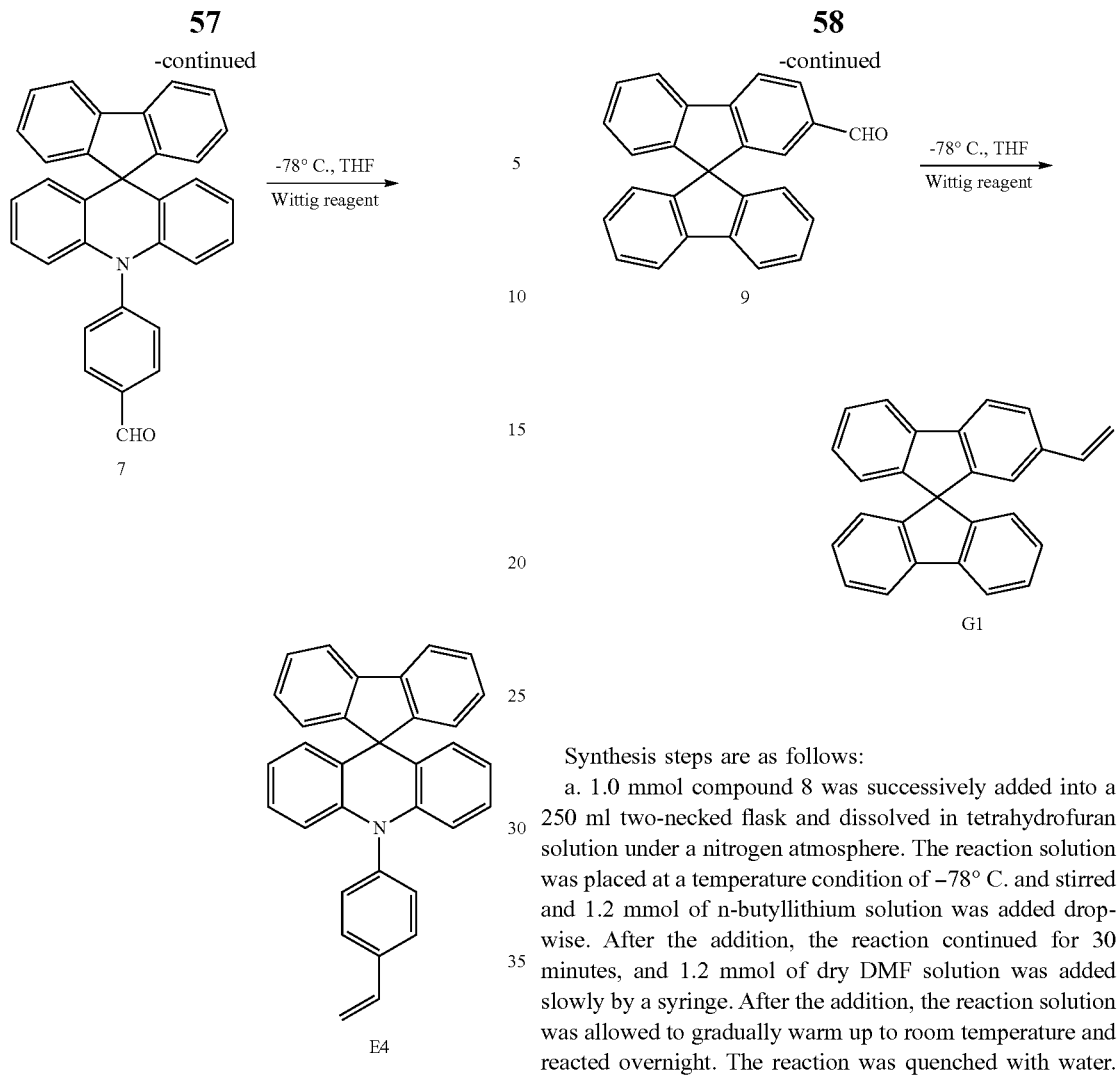

The synthesis steps of monomer E4 are similar to that of monomer E1, except that compound 6 was used in the first step and the subsequently resulting aldehyde-containing intermediate was compound 7. Finally, an intermediate E4 was obtained as a white solid powder. MS(APCI)=434.4.

(5) Synthesis of Monomer G1

An experimental synthetic route is shown as below:

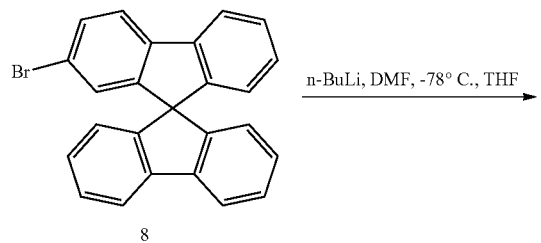

Synthesis steps are as follows:

a. 1.0 mmol compound 8 was successively added into a 250 ml two-necked flask and dissolved in tetrahydrofuran solution under a nitrogen atmosphere. The reaction solution was placed at a temperature condition of −78° C. and stirred and 1.2 mmol of n-butyllithium solution was added dropwise. After the addition, the reaction continued for 30 minutes, and 1.2 mmol of dry DMF solution was added slowly by a syringe. After the addition, the reaction solution was allowed to gradually warm up to room temperature and reacted overnight. The reaction was quenched with water. The reaction solution was extracted with dichloromethane, and the organic phase was washed with water. The organic phase was combined and dried over anhydrous sodium sulfate and the organic solvent was distilled off under a reduced pressure to give a crude product. The crude product was recrystallized from dichloromethane and n-hexane to give 0.88 mmol of a white solid powder 9, which was dried under vacuum for use. MS(APCI)=345.1.

b. 1.0 mmol of the compound 9 obtained above was dissolved in 200 ml of dry tetrahydrofuran (THF) solution. The reaction solution was placed at a temperature of −78° C. and stirred under the protection of a nitrogen atmosphere and 1.0 mmol of methylene triphenyl phosphorane (Wittig reagent) was added dropwise. After the addition, the reaction solution was allowed to gradually warm up to room temperature and continued to stir overnight at room temperature. The reaction was quenched with water. All the reaction solution was extracted with dichloromethane, and the organic phase was washed with water. Finally, the organic phase was combined, dried over anhydrous sodium sulfate, filtered and the organic solvent was distilled off. The resulting product was purified by silica gel column with mobile phase being dichloromethane: petroleum ether=1:1, to finally give 0.95 mmol of monomer G1, which was dried under vacuum for use. MS(APCI)=343.4.

(6) Synthesis of Monomer G2
An experimental synthetic route is shown as below:

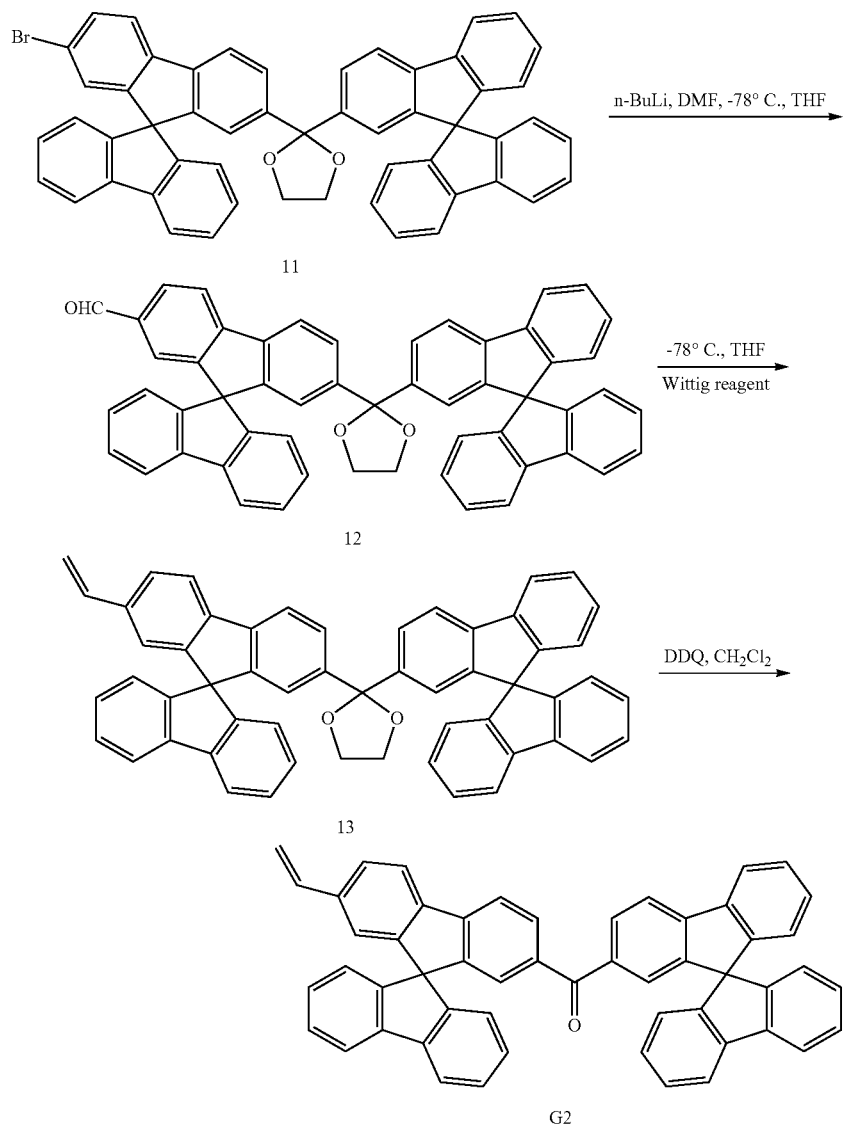

Synthesis steps are as follows:

The synthesis method and steps are similar to that of synthesis step a of monomer G1, and finally, an intermediate compound 12 was obtained;

The synthesis method and steps are similar to that of synthesis step b of monomer G1, and finally, an intermediate compound 13 was obtained;

c. 1.0 mmol of the intermediate compound 13 obtained in the above step was dissolved in 100 ml of dichloromethane solution under a nitrogen atmosphere, and 1.2 mmol of dichlorodicyanobenzoquinone (DDQ) was added. The reaction was stirred at room temperature for 4 hours and quenched with water. The organic phase was washed with water, and combined, dried over anhydrous sodium sulfate, filtered and the organic solvent was distilled off under a reduced pressure to give 0.92 mmol of a crude product G2. The crude product was recrystallized from dichloromethane and methanol to give a white solid powder, which was dried under vacuum for use. MS(APCI)=685.8.

(7) Synthesis of Monomer G3

An experimental synthetic route is shown as below:

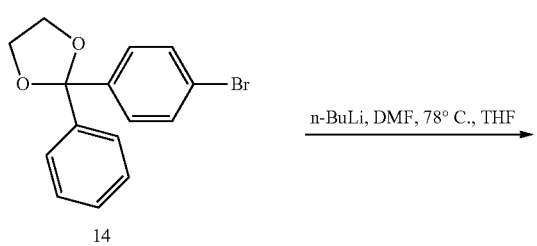

14

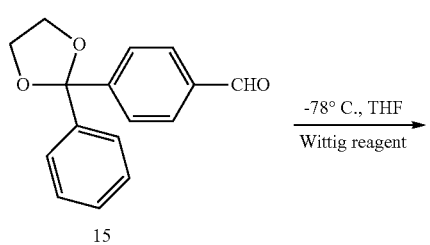

15

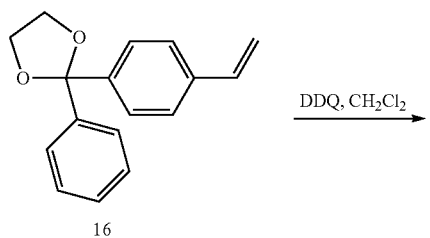

16

G3

The synthesis steps of monomer G3 are absolutely the same as that of monomer G1, except that compound 14 was used in the first step and the subsequently resulting aldehyde-containing intermediate was compound 15. Finally, by removing the protecting group, a final intermediate G3 was obtained as a white solid powder. MS(APCI)=209.4.

(8) Synthesis of Monomer G4

An experimental synthetic route is shown as below:

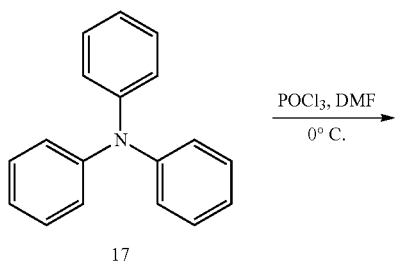

17

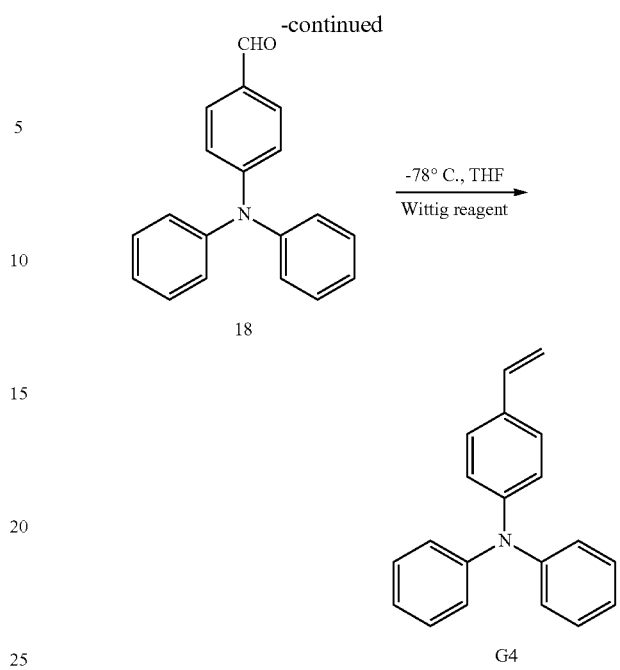

18

G4

The synthesis steps of monomer G4 are absolutely the same as that of monomer E1, except that compound 17 was used in the first step and the subsequently resulting aldehyde-containing intermediate was compound 18. Finally, a final intermediate G4 was obtained as a white solid powder. MS(APCI)=272.3.

(9) Synthesis of Monomer G5

An experimental synthetic route is shown as below:

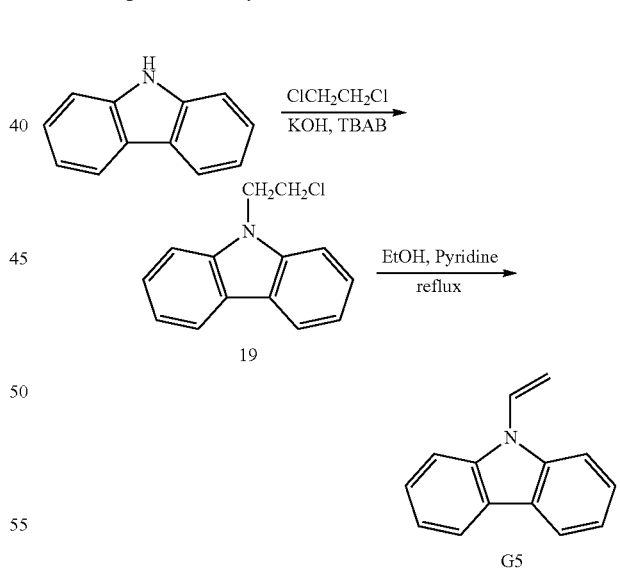

19

G5

Specific synthesis steps are as follows:

30 mmol carbazole, a certain weight of tri-n-butylammonium bromide (TBAB), 30 ml of a 50% aqueous solution of KOH and 50 ml of 1,2-dichloroethane were added into a three-necked flask equipped with a stirrer and a reflux condenser pipe and stirred vigorously at a temperature of 80° C. for 2 hours. The unreacted 1,2-dichloroethane was distilled off under a reduced pressure and the residue was poured into water to give a reddish-brown solid, which is filtered and recrystallized from ethanol to give a light red crystalline compound 19. MS (APCI)=230.4.

b. 10 mmol of compound 19 and pyridine were dissolved in absolute ethanol, refluxed for 30 minutes, allowed to settle down and cooled to separate white aciculate crystals out. The white crystals were separated from the reaction solution by a suction filtration and the residue was poured into water. The precipitate was collected and recrystallized from methanol to give 8.2 mmol of monomer G4 as a white solid, which was dried under vacuum for use. MS(APCI) =230.4.

The energy level of the organic repeating structural unit can be calculated by quantum, for example, by using TD-DFT (time-dependent density functional theory) by Gaussian09W (Gaussian Inc.), and specific simulation methods can be found in WO2011141110. Firstly, the molecular geometry is optimized by semi-empirical method "Ground State/Semi-empirical/Default Spin/AM1" (Charge 0/Spin Singlet). Then, the energy structure of organic molecules is determined by TD-DFT (time-density functional theory) Calculate "TD-SCF/DFT/Default Spin/B3PW91" and the base group "6-31G (d)" (Charge 0/Spin Singlet). The HOMO and LUMO levels are calculated using the following calibration formula: Si and T1 are used directly.

$$HOMO(eV)=((HOMO(G) \times 27.212)-0.9899)/1.1206$$

$$LUMO(eV)=((LUMO(G) \times 27.212)-2.0041)/1.385$$

Where HOMO (G) and LUMO (G) are the direct results of Gaussian 09W, in units of Hartree. The results are shown in Table 1:

TABLE 1

| | Structural unit | | | | |
|---|---|---|---|---|---|
| | HOMO [eV] | LUMO [eV] | S1 [eV] | T1 [eV] | S1 − T1 [eV] |
| E1 | −5.58 | −2.78 | 2.83 | 2.79 | 0.04 |
| E2 | −5.54 | −2.82 | 2.84 | 2.79 | 0.05 |
| E3 | −5.32 | −2.91 | 2.48 | 2.39 | 0.09 |
| E4 | −5.75 | −3.15 | 2.52 | 2.51 | 0.01 |
| G1 | −5.87 | −1.49 | 4.06 | 2.96 | 1.10 |
| G2 | −5.92 | −2.52 | 3.38 | 2.58 | 0.80 |
| G3 | −6.64 | −2.43 | 3.49 | 2.84 | 0.65 |
| G4 | −5.19 | −0.91 | 3.73 | 3.01 | 0.73 |
| G5 | −5.70 | −1.32 | 4.11 | 3.12 | 0.99 |

3. Synthesis of Polymer

The main synthesis steps for the synthesis of polymers are as follows: taking the synthesis of P1 polymer for example, monomers of 0.15 mmol of E1, 0.50 mmol of G1 and 0.35 mmol of G5 were dissolved in benzene solvent under the protection of nitrogen while 0.01 mmol of (2,2-azobisisobutyronitrile (AIBN initiator) was added by a syringe; the reaction solution was sealed and reacted at 60° C. for 4 hours. After the reaction, the reaction solution was cooled to room temperature and the polymer was precipitated out with methanol. The precipitate was dissolved in tetrahydrofuran (THF) and precipitated with methanol again. This was Repeated from 3 to 5 times and the product was dried under vacuum to give a solid of polymer P1.

The synthesis steps for P2-P8 are similar to that of P1, except for containing different proportions of vinyl monomer. The monomers and proportions contained in P2 P8 are shown in the following table:

| Polymer | E1 | E2 | E3 | E4 | G1 | G2 | G3 | G4 | G5 |
|---|---|---|---|---|---|---|---|---|---|
| P1 | 15 | | | | 50 | | | | 35 |
| P2 | | 15 | | | 50 | | | | 35 |
| P3 | | | 15 | | 50 | | | | 35 |
| P4 | | | | 15 | 50 | | | | 35 |
| P5 | | | | 15 | 50 | 35 | | | |
| P6 | 15 | | | | 50 | | | 35 | |
| P7 | 15 | | | | 50 | | 35 | | |
| P8 | | 15 | | | 50 | 35 | | | |

3. Preparation and Measurement of OLED Devices:

The preparation process of the OLED devices above will be described in detail with reference to specific examples below. The structure of the OLED devices is as follows: ITO/HIL/HTL/EML/ETL/cathode. The preparation steps are as follows:

a, cleaning of ITO (indium tin oxide) conductive glass substrate: washing with the use of various solvents (such as one or more of chloroform, acetone or isopropyl alcohol) and then treating with UV and ozone;

b. HIL (hole-injecting layer, 60 nm): 60 nm PEDOT (polyethylenedioxythiophene, Clevios™ AI4083) was obtained by spin-coating as an HIL in an ultra clean chamber, and treated on a hot plate at 180° C. for 10 minutes;

c. HTL (hole-transporting layer, 20 nm): 20 nm TFB or PVK (Sigma Aldrich, having an average Mn of 25,000-50,000) was obtained by spin-coating in a nitrogen glove box, and the solution used was TFB or PVK added into a toluene solvent, with a solubility of solution of 5 mg/ml, followed by a treatment on a hot plate at 180° C. for 60 minutes;

wherein TFB (H.W. SandsCorp.) is a hole-transporting material for HTL, its structure is as follows:

d. EML (organic light emitting layer): EML was formed by spin-coating in a nitrogen glove box and the solution used was the polymer (P1-P8) added into a toluene solvent, with a solubility of solution of 10 mg/ml, followed by a treatment on a hot plate at 180° C. for 60 minutes. The component and thickness of EML of the devices are listed in Table 2.

TABLE 2

| OLED device | HTL | Component and thickness of EML |
|---|---|---|
| OLED1 | PVK | P1(65 nm) |
| OLED2 | PVK | P2(65 nm) |
| OLED3 | TFB | P3(80 nm) |
| OLED4 | TFB | P4(80 nm) |
| OLED5 | TFB | P5(80 nm) |
| OLED6 | PVK | P6(65 nm) |
| OLED7 | PVK | P7(65 nm) |
| OLED8 | TFB | P8(65 nm) | e, cathode: Ba/Al (2 nm/100 nm) in high vacuum ($1 \times 10^{-6}$ mbar) in the thermal deposition;

f, package: device in the nitrogen glove box with UV curing resin package.

The current-voltage (J-V) and luminescence characteristics of each OLED device are characterized by characterization equipment, while recording important parameters such as efficiency, lifetime and driving voltage. The performance of OLED devices is summarized in Table 3.

TABLE 3

| OLED device | colour | V@1 knits [V] | current efficiency @ 1 knits [Cd/A] |
|---|---|---|---|
| OLED1 | blue-green | 8.5 | 16 |
| OLED2 | blue-green | 8.3 | 18 |
| OLED3 | green | 7.1 | 35 |
| OLED4 | yellow-green | 7.5 | 32 |
| OLED5 | yellow-green | 6.8 | 38 |
| OLED6 | blue-green | 7.9 | 14 |
| OLED7 | blue-green | 7.6 | 19 |
| OLED8 | green | 6.7 | 43 |

The invention claimed is:

1. A polymer having the following general structural formula:

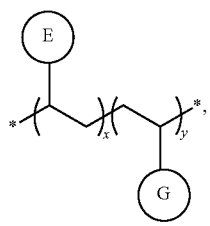

wherein E is a structural unit,
the energy difference between the singlet energy level and the triplet energy level of the structural unit E, i.e. (S1(E)–T1(E)), is less than or equal to 0.35 eV,
x and y are the molar fractions,
x+y=1, and
G is an organic functional group selected from the group consisting of a hole-injecting or hole-transporting group, a hole-blocking group, an electron-injecting or electron-transporting group, an electron-blocking group, an organic host group, a singlet emitter group, and a triplet emitter group.

2. The polymer according to claim 1, wherein (S1(E)–T1(E))≤0.25 eV.

3. The polymer according to claim 1, wherein the structural unit E contains at least one electron donating group D and at least one electron accepting group A.

4. The polymer according to claim 1, wherein the structural unit E contains a structural unit represented by the structural formula (I):

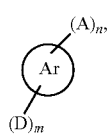
(I)

where Ar is an aromatic or heteroaromatic structural unit,
D is an electron donating group,
A is an electron accepting group,
each of n and m is an integer between 1 and 6,
when m>1, each D is independently selected from the same or different electron donating groups, and
when n>1, each A is independently selected from the same or different electron accepting groups.

5. The polymer according to claim 3, wherein the electron donating group D is selected from structural units containing any one of the following groups:

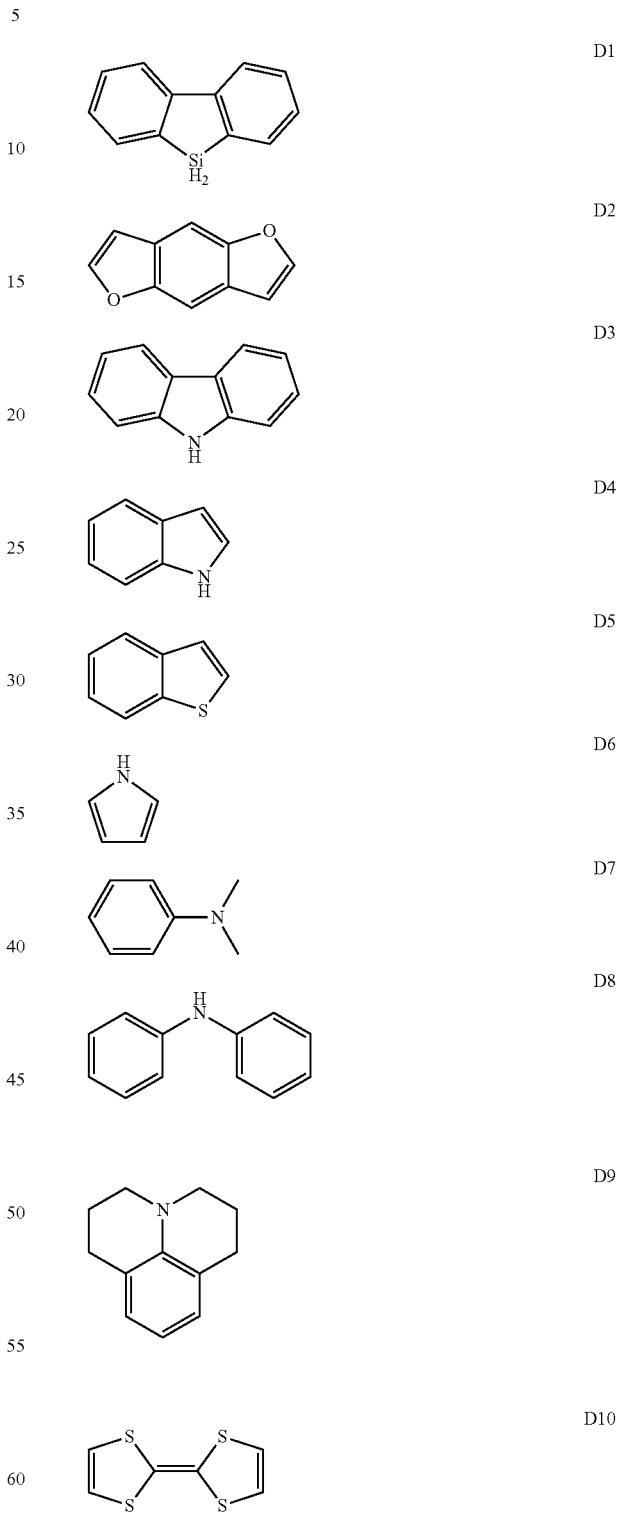

6. The polymer according to claim 3, wherein the electron accepting group A is selected from the group consisting of F, cyano group, and structural units containing any one of the following groups:

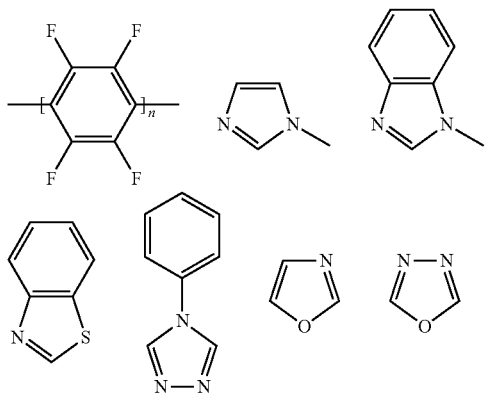
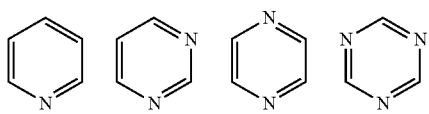
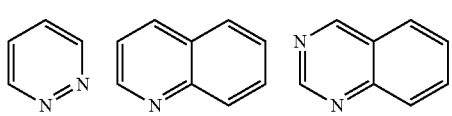
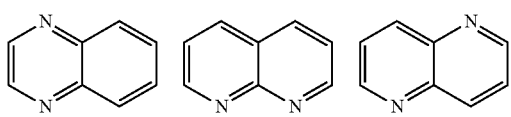
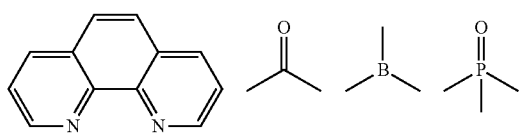
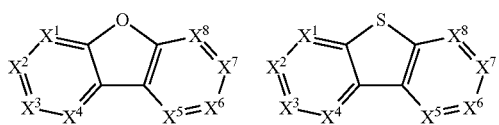

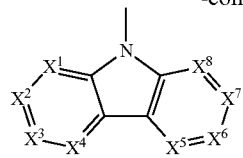

wherein n1 is an integer from 1 to 3, $X^1$-$X^8$ are $CR^1$ or N, at least one of $X^1$-$X^8$ is N, and $R^1$ is selected from the group consisting of hydrogen, alkyl, alkoxy, amino, alkenyl, alkynyl, aralkyl, heteroalkyl, aryl, and heteroaryl.

7. The polymer according to claim 4, wherein Ar is selected from structural units containing any one of the following groups:

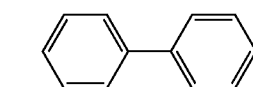
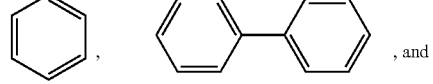
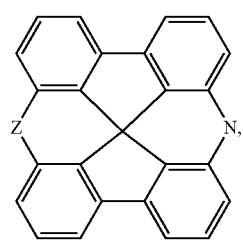

where z is O or S.

8. The polymer according to claim 1, wherein the structural unit E is selected from structural units containing any one of the following structural formulas:

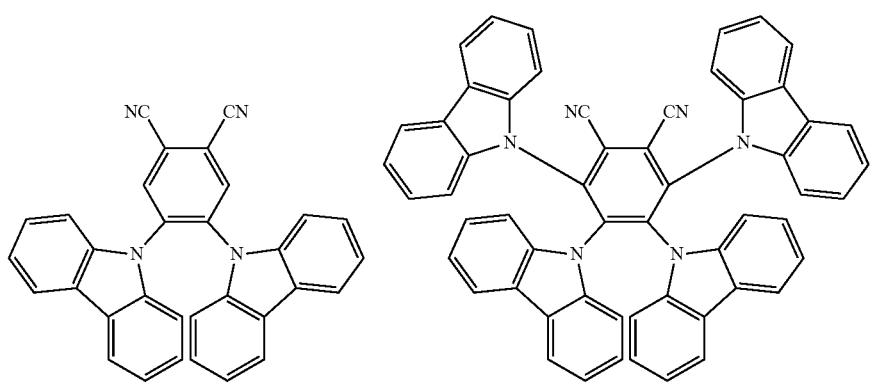

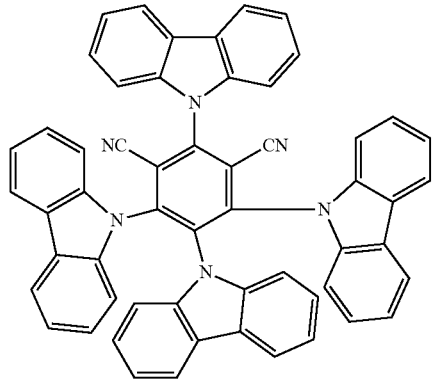
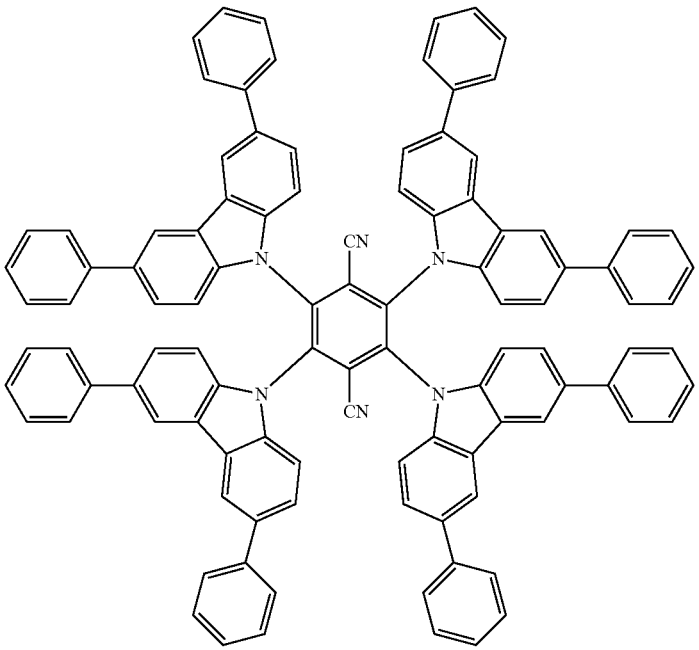
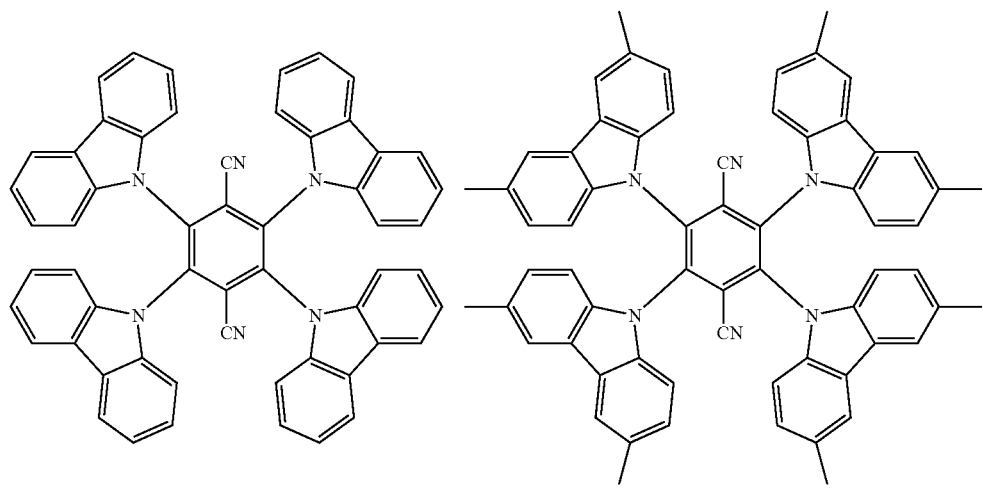
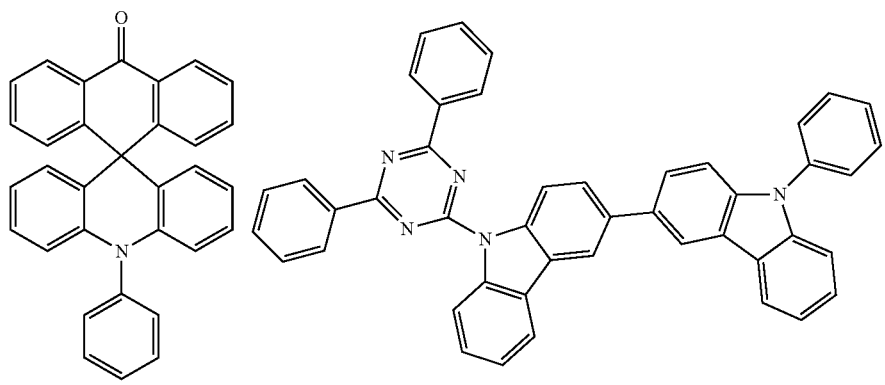

-continued
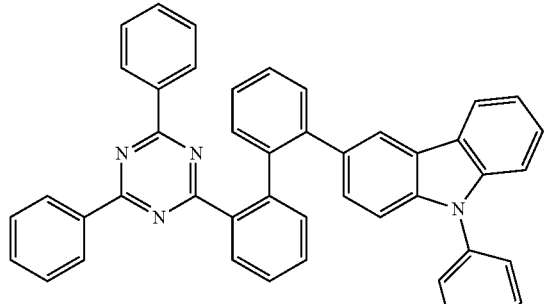
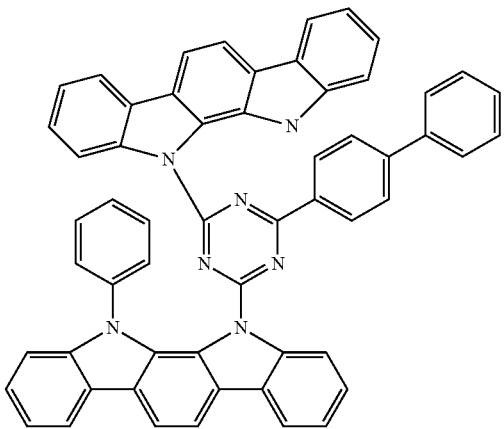
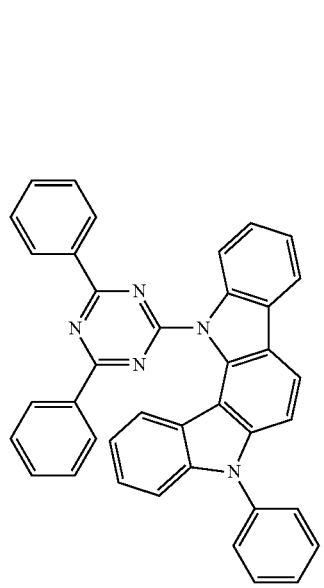
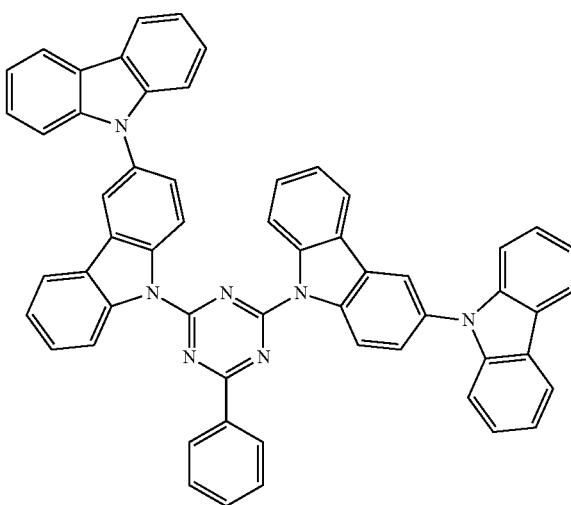
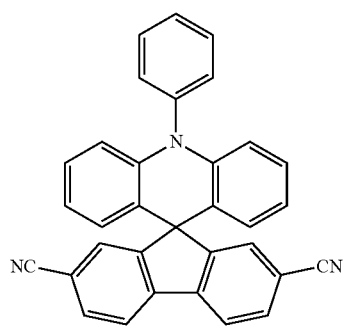
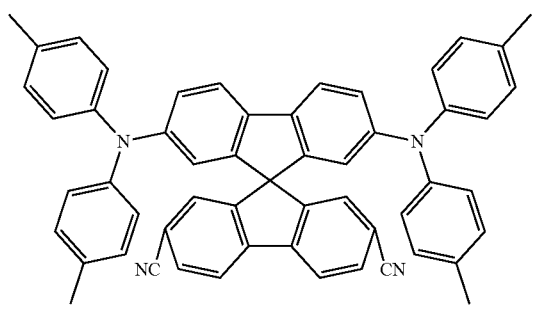

-continued

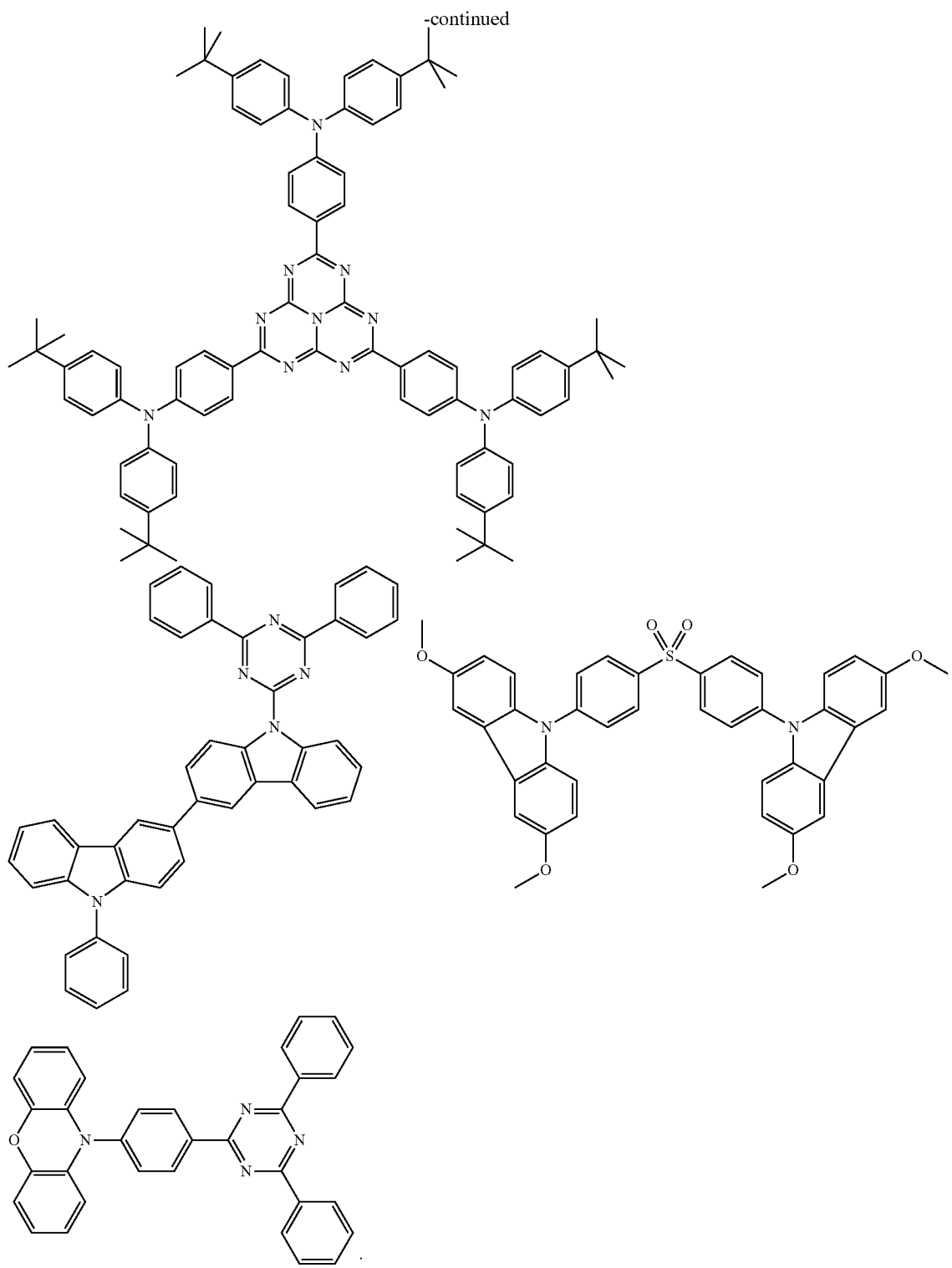

9. A mixture, comprising:
the polymer according to claim 1; and
at least one organic functional material that is selected from the group consisting of a hole-injecting or hole-transporting material, a hole-blocking material, an electron-injecting or electron-transporting material, an electron-blocking material, an organic host material, a singlet emitter, and a triplet emitter.

10. The mixture according to claim 9, wherein the at least one organic functional material is a singlet emitter or a triplet emitter.

11. A formulation comprising the polymer according to claim 1 and at least one organic solvent.

* * * * *